US012797561B2

(12) United States Patent
Lastow et al.

(10) Patent No.: US 12,797,561 B2
(45) Date of Patent: Nov. 17, 2026

(54) DRY POWDER INHALER

(71) Applicant: Iconovo AB, Lund (SE)

(72) Inventors: Orest Lastow, Torna Haellestad (SE); Calo Ahlgren, Malmo (SE); Fredrik Gunnarsson, Soedra Sandby (SE); Magnus Waldt, Kaevlinge (SE); Simon Karlsson, Lund (SE)

(73) Assignee: Iconovo AB (SE)

(*) Notice: Subject to any disclaimer, the term of this patent is extended or adjusted under 35 U.S.C. 154(b) by 629 days.

(21) Appl. No.: 18/274,713

(22) PCT Filed: Jan. 27, 2022

(86) PCT No.: PCT/SE2022/050084

§ 371 (c)(1),
(2) Date: Jul. 27, 2023

(87) PCT Pub. No.: WO2022/164372

PCT Pub. Date: Aug. 4, 2022

(65) Prior Publication Data

US 2025/0082872 A1 Mar. 13, 2025

(30) Foreign Application Priority Data

Jan. 28, 2021 (SE) .................................... 2150094-7

(51) Int. Cl.
*A61M 15/00* (2006.01)

(52) U.S. Cl.
CPC .... *A61M 15/0003* (2014.02); *A61M 15/0043* (2014.02); *A61M 15/0048* (2014.02);
(Continued)

(58) Field of Classification Search
CPC .......... A61M 15/0003; A61M 15/0043; A61M 15/0048; A61M 15/0036; A61M 15/0041;
(Continued)

(56) References Cited

U.S. PATENT DOCUMENTS

2005/0103337 A1* 5/2005 Hickey ............. A61M 15/0023 128/203.15
2007/0181124 A1 8/2007 Casper
(Continued)

FOREIGN PATENT DOCUMENTS

CA 2382502 A1 3/2001
DE 202012003962 U1 5/2012
(Continued)

OTHER PUBLICATIONS

English abstract for DE-202012003962.
(Continued)

*Primary Examiner* — Tu A Vo
*Assistant Examiner* — Kelsey E Baller
(74) *Attorney, Agent, or Firm* — Fishman Stewart PLLC

(57) ABSTRACT

A dry powder inhaler includes at least one inlet, at least one outlet, and a dosage mechanism between the at least one inlet and the at least one outlet for arranging a dose of a dry powder medicament such that the dose may be delivered upon inhalation at the at least one outlet. The dosage mechanism includes a dose wheel configured to retain a plurality of medicament cavities for housing the dry powder medicament. The dosage mechanism further includes a dosing element movable between an inactive position and a dose-administering position. The dosing element is configured to enable fluid communication between at least one medicament cavity and the at least one outlet when in the dose-administering position.

18 Claims, 16 Drawing Sheets

(52) U.S. Cl.
CPC ................. *A61M 2202/064* (2013.01); *A61M 2205/0238* (2013.01); *A61M 2209/045* (2013.01)

(58) Field of Classification Search
CPC ........ A61M 15/0026; A61M 2202/064; A61M 2205/0238; A61M 2209/045; A61M 2207/00; B65B 69/0058
See application file for complete search history.

(56) References Cited

U.S. PATENT DOCUMENTS

| | | | | |
|---|---|---|---|---|
| 2007/0221216 | A1* | 9/2007 | Ganem ............. | A61M 15/0028 128/200.24 |
| 2007/0221218 | A1* | 9/2007 | Warden ............. | A61M 15/0085 128/203.15 |
| 2008/0283056 | A1 | 11/2008 | Rohrschneider | |
| 2009/0114220 | A1 | 5/2009 | Wachtel | |
| 2010/0078022 | A1 | 4/2010 | Striebig | |
| 2010/0083962 | A1 | 4/2010 | Von Schuckmann | |
| 2010/0300442 | A1* | 12/2010 | Houzego ........... | A61M 15/0061 128/203.15 |
| 2010/0326440 | A1* | 12/2010 | Lastow ............. | A61M 15/0043 128/203.21 |
| 2011/0186047 | A1* | 8/2011 | Lewis ............... | A61M 15/0075 128/203.15 |
| 2012/0048272 | A1 | 3/2012 | Briant | |
| 2012/0111327 | A1 | 5/2012 | Smith | |
| 2012/0298107 | A1 | 11/2012 | Houzego | |
| 2020/0139059 | A1* | 5/2020 | Giraud .............. | A61M 15/0045 |

FOREIGN PATENT DOCUMENTS

| | | | |
|---|---|---|---|
| EP | 2451514 | A1 | 5/2012 |
| EP | 3042681 | A1 | 7/2016 |
| WO | 2006071512 | A1 | 7/2006 |
| WO | 2007118490 | A1 | 10/2007 |
| WO | 2010052479 | A1 | 5/2010 |
| WO | 2011004287 | A1 | 1/2011 |
| WO | 2012128692 | A1 | 9/2012 |
| WO | 2015080653 | A1 | 6/2015 |

OTHER PUBLICATIONS

Swedish Search Report for SE-2150094-7, dated Jan. 28, 2021.
European Search Report dated Dec. 18, 2024 for European Patent Application 22746353.6.

* cited by examiner

DRY POWDER INHALER

CROSS-REFERENCE TO RELATED APPLICATIONS

This application claims priority to International Patent Application No. PCT/SE2022/050084 filed on Jan. 27, 2022, which also claims priority to Swedish Patent Application No. SE 2150094-7 filed Jan. 28, 2021, the contents of each of which is hereby incorporated by reference in its entirety.

TECHNICAL FILED

The present application relates to medicament inhalers and in particular to inhalers for delivery of dry powder medicaments to a user.

BACKGROUND

Inhalers have been widely used in the pharmaceutical field for treatment of respiratory and/or other diseases. Numerous drugs, medications and other substances are inhaled into the lungs using the inhalers for rapid absorption of the drug etc. in the blood stream and for local action in the lung.

Inhaled drugs fall into two main categories, one being in the form of liquids, including suspensions, and the other being powders. The choice of liquids or powders depends on the characteristics of the drugs, medications, etc. to be inhaled.

The most common type of inhaler is the pressurized metered-dose inhaler. In this type of inhaler, medication is most commonly stored in solution in a pressurized canister that contains a propellant, although it may also be a suspension. The canister is attached to a plastic, hand-operated actuator. On activation, the metered-dose inhaler releases a fixed dose of medication in aerosol form. Another type of inhaler is a nebulizer, which supplies medication as an aerosol created from an aqueous formulation.

Another type of inhaler is a dry powder inhaler. A dry powder inhaler releases a measured dose of powdered medication that is inhaled through a mouthpiece of the inhaler. Often, the measured dose is stored in one of a number of cavities inside the inhaler, for example in a blister pack. Each cavity has a pierceable cover that can be pierced to release the medication prior to inhalation by the user. Cavity-based dry powder inhalers provide good hygiene as well as ensuring that the proper dose of medicament is provided to the user.

However, certain issues persist with cavity-based dry powder inhalers. In some implementations, it is desired to deliver more than one medicament in a combined dose. However, it may not be suitable to store two or more medicaments in a single cavity. Therefore, separate cavities are used for different medicaments. In these cases, it can be challenging to ensure that the two or more separate medicaments are properly deaggregated and mixed to be provided to a user in a single dose. It can also be difficult to ensure that two cavities are opened simultaneously for delivery in a combined dose, especially in a repeatable manner. Existing solutions involve complex mechanisms and do not achieve the desired delivery characteristics.

SUMMARY

The dry powder inhalers disclosed herein provide a dosing mechanism having a dose wheel and a dosing element that allow two medicament cavities to be simultaneously accessed for delivery in a combined dose. The dosing element acts both as a mechanism for accessing the medicament inside the cavities and delivering it to the user. This allows medicaments from two separate cavities to be deaggregated and mixed properly before inhalation by a user. The mechanism allows such doses to be delivered in a repeatable manner. The mechanism has a simpler construction than those currently known for providing combined doses of multiple medicaments.

The methods of packaging dry powder medicaments disclosed herein, and the packaging produced by such methods, provide for filling a number of cavities in a linear row, before being assembled into an inhaler. This allows multiple cavities to be easily filled and sealed such that they can be provided in a combined dose, especially compared to doing so when the cavities are arranged in the annular form in which the packaging is assembled into an inhaler. The packaging also provides protection against, for example, humidity, as the seals serve as barriers from the outside.

According to an aspect, there is provided a dry powder inhaler comprising: at least one inlet; at least one outlet; and a dosage mechanism between the at least one inlet and the at least one outlet for arranging a dose of a dry powder medicament such that the dose may be delivered upon inhalation at the outlet, wherein the dosage mechanism comprises: a dose wheel configured to retain a plurality of medicament cavities for housing a dry powder medicament; and a dosing element movable between an inactive position and a dose-administering position, the dosing element configured to enable fluid communication between at least one of the medicament cavities and the outlet when in the dose-administering position.

Optionally, the dose wheel is configured to rotate relative to the dosing element between a plurality of dose delivery positions. Optionally, each dose delivery position corresponds to an alignment between one or more medicament cavities and the dosing element. Optionally, each dose delivery position corresponds to an alignment between two medicament cavities and the dosing element.

Optionally, the dry powder inhaler further comprises a gear system configured to rotate the dose wheel relative to the dosing element and/or actuate the dosing element between the inactive position and the dose-administering position. Optionally, in the inactive position, the dosing element is arranged within the dose wheel. Optionally, the gear system comprises a first gear mechanism and a second gear mechanism, the first gear mechanism is configured to rotate the dose wheel, the second gear mechanism is configured to actuate the dosing element, and the first gear mechanism and the second gear mechanism are configured to interact such that the rotation of the dose wheel and the actuation the dosing element are provided in the same action.

Optionally, the dosing element comprises a manifold arranged to provide fluid communication between the inlet and at least one of the medicament cavities and between the at least one of the medicament cavities and the outlet when in the dose-administering position. Optionally, the manifold comprises at least one first conduit and at least one second conduit, wherein, when in the dose-administering position the at least one first conduit is arranged to provide fluid communication between at least one medicament cavity and the at least one second conduit, and the at least one second conduit is arranged to provide fluid communication between the at least one first conduit and the outlet. Optionally, the manifold comprises two first conduits, each arranged to provide fluid communication between a respective medicament cavity and the at least one second conduit when in the dose-administering position. Optionally, the manifold comprises two second conduits, each arranged to provide fluid communication between the at least one first conduit and the outlet when in the dose-administering position. Optionally, the manifold further comprises at least one third conduit arranged to provide fluid communication between the inlet and the at least one first conduit and/or between the inlet and the at least one second conduit when in the dose-administering position.

Optionally, each medicament cavity is sealed by a sealing element, and wherein the dosing element is configured to at least partially remove the sealing element from at least one medicament cavity when moving from the inactive position to the dose-administering position to enable fluid communication between the at least one medicament cavity and the outlet when in the dose-administering position. Optionally, the dosing element is configured to at least partially remove the sealing element from two medicament cavities simultaneously when moving from the inactive position to the dose-administering position to enable fluid communication between the two medicament cavities and the outlet when in the dose-administering position. Optionally, the sealing element is a film or foil. Optionally, the dosing element is configured to at least partially remove the sealing element by peeling the sealing element from the at least one medicament cavity when moving from the inactive position to the dose-administering position.

BRIEF DESCRIPTION OF THE DRAWINGS

Exemplary embodiments of the disclosure shall now be described with reference to the drawings in which.

Throughout the description and the drawings, like reference numerals refer to like parts.

DETAILED DESCRIPTION

Figure 1:
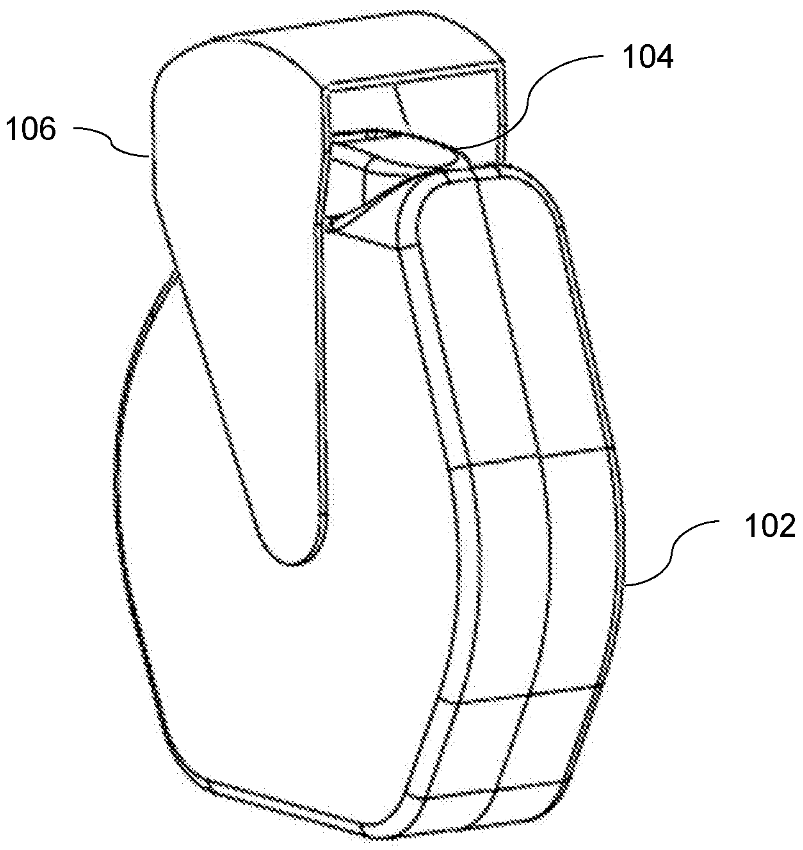
FIG. 1 shows an inhaler according to the disclosure.

FIG. 1 shows an inhaler 100 according to the disclosure. The inhaler 100 comprises a housing 102, a mouthpiece 104 and a cover 106. The housing 102 contains components that allow delivery of a drug to a user, as will be explained in relation to FIG. 2. The mouthpiece 104 comprises at least one outlet that provides fluid communication between the inside of the inhaler 100 and the user during an inhalation. The cover 106 covers the mouthpiece 104 when the inhaler 100 is not in use. The cover 106 may be connected to the housing 102 such that it can be moved from a first position covering the mouthpiece 104 to a second position where the mouthpiece 104 is accessible by the user. For example, the cover 106 may be rotatably connected to the housing 102. In some implementations, the angle between the first position and the second position is 90°. When the cover 106 is in the open second position, the user may put their mouth over the mouthpiece 104 and inhale a medicament that is stored inside the inhaler 104.

Figure 2:
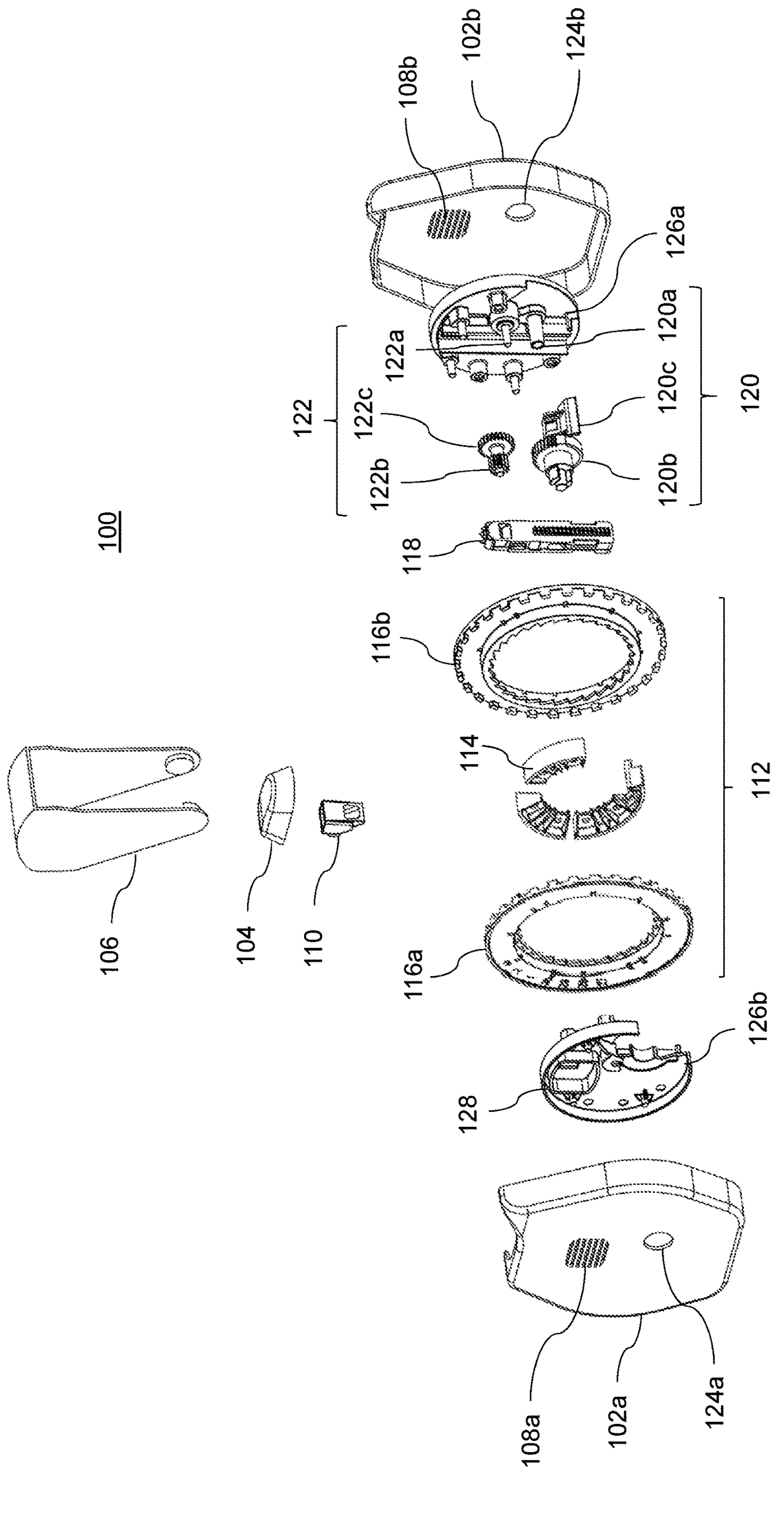
FIG. 2 shows an exploded view of an inhaler according to the disclosure.

FIG. 2 shows an exploded view of an inhaler, for example the inhaler 100. As shown in FIG. 2, the housing 102 comprises a front portion 102*a* and a rear portion 102*b*, between which are assembled a number of components that allow delivery of a drug to a user via the mouthpiece 104.

The front portion 102*a* comprises a first inlet 108*a* and the rear portion 102*b* comprises a second inlet 108*b*. The inlets 108*a-b* may take the form of a grille, as shown in FIG. 2, or other type of hole or aperture that allows air to pass from outside the housing 102 to the inside. It will be appreciated that the location and configuration of the inlets 108 can be different to that shown in FIG. 2. For example, only one portion of the housing 102 may comprise an inlet 108. In another example, one portion of the housing 102 may comprise a plurality of inlets 108. In another example, both portions of the housing 102 may comprise a plurality of inlets 108. In some implementations, the inlet 108 may be part of the mouthpiece 104. Other suitable implementations of inlets that allow air to pass from outside the housing 102 to the inside will be readily envisaged by the skilled person.

The mouthpiece 104 comprises at least one outlet that allows air to travel outwardly from inside the housing 102. The user may inhale at the outlet of the mouthpiece 104, such that the air is drawn into the inlets 108*a-b*, entrains dry powder medicament from inside the housing 102, and passes through the outlet to be inhaled by the user. This will be explained in more detail in relation to FIGS. 3A to 3E and 4A to 4E. A duct 110 may be provided in order to provide fluid communication between the mouthpiece 104 and the inside of the housing 102.

The inhaler 100 comprises a dosage mechanism arranged inside the housing 102. The dosage mechanism comprises a dose wheel 112 and a dosing element 118. The dosage mechanism arranges a dose of dry powder medicament such that the dose may be delivered to the user upon inhalation at the outlet of the mouthpiece 104.

The dose wheel 112 comprises a base 114 and a pair of medicament-retaining brackets 116*a-b*. The dose wheel 112 is configured to retain a plurality of medicament cavities housing dry powder medicament. The plurality of medicament cavities may be in the form of a blister strip or the like. In some examples, the plurality of medicament cavities is in the form of an annular packaging as described in relation to FIGS. 5 to 8. The base 114 serves as a spacer to maintain the annular form and keep the cavities at a fixed distance from each other. The medicament-retaining brackets 116*a-b* hold the plurality of medicament cavities in place and provide rotation of the dose wheel 112, as will be discussed below. In particular, the brackets 116*a-b* may be rotatable relative to the base 114. In some implementations, the brackets 116*a-b* may hold the medicament cavities in place sufficiently that the base 114 is not required.

In some implementations, the dose wheel 112 is configured to rotate in tandem with the assembled medicament cavities about a common central axis. For example, the medicament-retaining brackets 116*a-b* may hold a plurality of medicament cavities in place, and the brackets 116*a-b* and the cavities rotate in tandem. The rotation may be between a plurality of dose delivery positions. Each dose delivery position may correspond to an alignment between one or more of the medicament cavities and the dosing element 118 and/or the mouthpiece 104. As such, when the dose wheel 112 is in a dose delivery position, dry powder medicament may be passed from at least one medicament cavity to the user via the dosing element 118 and the mouthpiece 104, as will be explained in relation to FIGS. 4A to 4E. In some examples, each dose delivery position corresponds to an alignment between two medicament cavities and the dosing element 118 and/or the mouthpiece 104.

The dosing element 118 is configured to enable fluid communication between at least one of the medicament cavities and the outlet of the mouthpiece 104 during an inhalation by the user. To enable this, the dosing element 118 can be actuated between an inactive position and a dose-administering position where the dosing element 118 is in fluid communication with the outlet of the mouthpiece 104. This will be explained in more detail in relation to FIGS. 3A to 3E and 4A to 4E. In some examples, the inactive position is within the dose wheel 112. That is to say, in the inactive position, the dosing element 118 is located inside the circumference of the dose wheel 112. In these implementations, the base 114 may comprise an opening such that the dosing element 118 can pass through the base 114 when moving between the inactive position and the dose-administering position.

Rotation of the dose wheel 112 and movement of the dosing element 118 are enabled by a gear system comprising a first gear mechanism 120 and a second gear mechanism 122. The first gear mechanism comprises a gear shaft 120*a*, a gear wheel 120*b* and a tab 120*c*. The second gear mechanism comprises a gear shaft 122*a*, a first gear wheel 122*b* and a second gear wheel 122*c*. The gear wheel 120*b* of the first gear mechanism 120 interacts with the first gear wheel 122*b* of the second gear mechanism 122. The tab 120*c* of the first gear mechanism 120 interacts with corresponding teeth on the brackets 116*a-b*. The second gear wheel 122*c* of the second gear mechanism 122 interacts with corresponding teeth on the dosing element 118. The gear mechanisms 120, 122 extend through holes in the dose wheel 112. A hole 124*a* in the front portion 102*a* of the housing 102 enables connection of the first gear mechanism 120 to a joint of the cover 106. A corresponding hole 124*b* may also be present in the rear portion 102*b* of the housing 102, for connection of the cover 106 to the first gear mechanism 120.

When the cover 106 is moved from the first position covering the mouthpiece 104 to the second position where the mouthpiece 104 is accessible by the user, the gear wheel 120*b* and tab 120*c* of the first gear mechanism 120 are rotated about the gear shaft 120*a*. As the gear wheel 120*b* is rotated about the gear shaft 120*a*, the interaction between the gear wheel 120*b* and the first gear wheel 122*b* of the second gear mechanism 122 causes the first gear wheel 122*b* and the second gear wheel 122*c* to be rotated about the gear shaft 122*a*. The interaction between the second gear wheel 122*c* and the dosing element 118 then causes translational movement of the dosing element 118 between an inactive position and a dose-administering position. When the cover 106 is moved back from the second position to the first position, the interaction between the tab 120*c* of the first gear mechanism 120 and the teeth of the brackets 116*a-b* causes rotation of the dose wheel 112 between a first dose delivery position and a second dose delivery position. As such, a single gear system enables both rotation of the dose wheel 112 and movement of the dosing element 118 in a single action of the cover 106.

The gear shafts 120*a* and 122*a* are mounted on a first plate 126*a*. The first plate 126*a*, and a second plate 126*b*, are configured to be connected and serve to hold the dose wheel 112 in position during rotation. This can be achieved by interaction between holes in the base 114 and the shafts mounted on the first plate 126*a*. The second plate 126*b* comprises an opening 128, which enables air to be drawn through the inlets 108*a-b* and into the dosage mechanism during an inhalation.

Once the gear wheel 112 is assembled with the gear mechanisms 120, 122 and the first and second plates 126*a-b*, the housing 102 may be closed to provide the assembled inhaler 100.

FIGS. 3A to 3E show the dosing mechanism, and in particular the actuation of the dose wheel 112 and the dosing element 118 by the gear mechanisms 120, 122. In each of FIGS. 3A to 3E, the dosing mechanism is shown with the medicament cavities present, but the housing 102, base 114, one bracket 116*b* and plates 126*a-b* removed. The dosing mechanism is shown in profile on the left and in cross-section on the right.

Figure 3A:
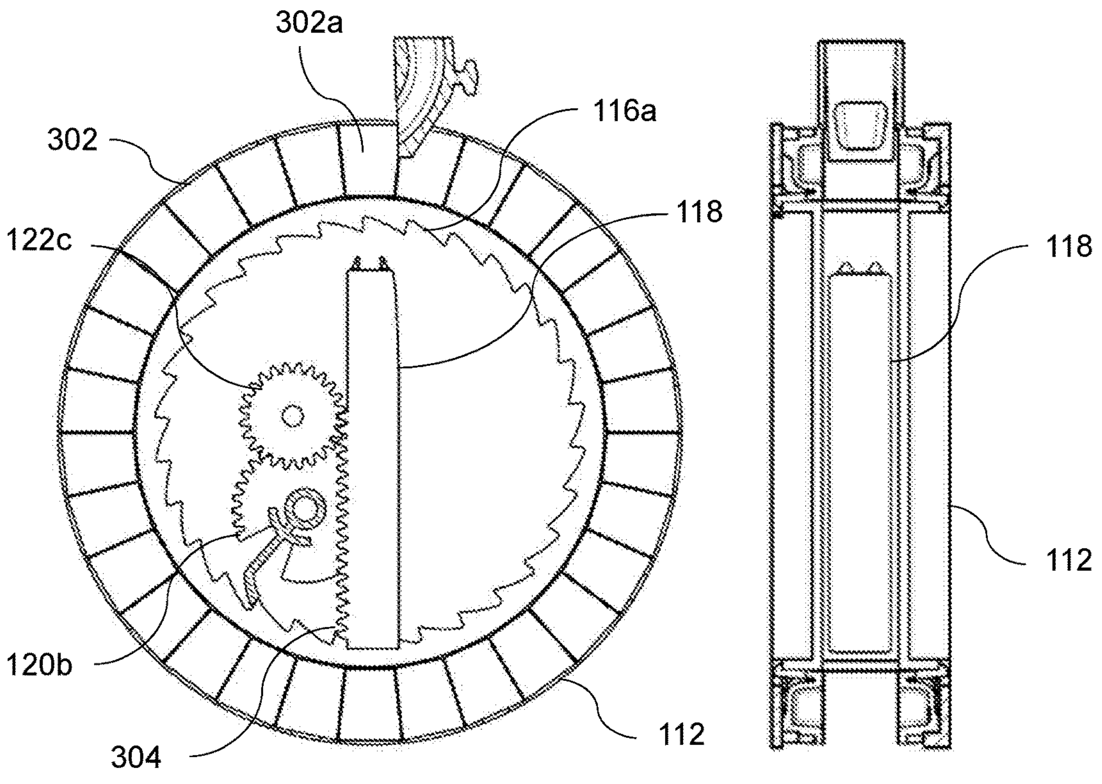
FIGS. 3A to 3E show a dosing element actuated by a gear mechanism according to the disclosure.

In FIG. 3A, the cover 106 (not shown) is in the first position covering the mouthpiece 104 and the dosing element 118 is in the inactive position. In this implementation, the inactive position is located within the dose wheel 112. Medicament cavities 302 are assembled on the dose wheel 112 and held in place by the brackets 116*a-b* of the dose wheel 112, as will be explained in relation to FIGS. 7 and 8A to 8D. In FIG. 3A, the dose wheel 112 is in a first dose delivery position, such that a first pair of medicament cavities 302*a* are aligned with the dosing element 118. Teeth of the second gear wheel 122*c* of the second gear mechanism 122 interact with teeth 304 of the dosing element 118, such that movement of the second gear mechanism 122 will cause movement of the dosing element 118. In some implementations, the cover 106 may be rotated up to 20° from the first position without actuation of the gear mechanisms 120, 122.

Figure 3B:
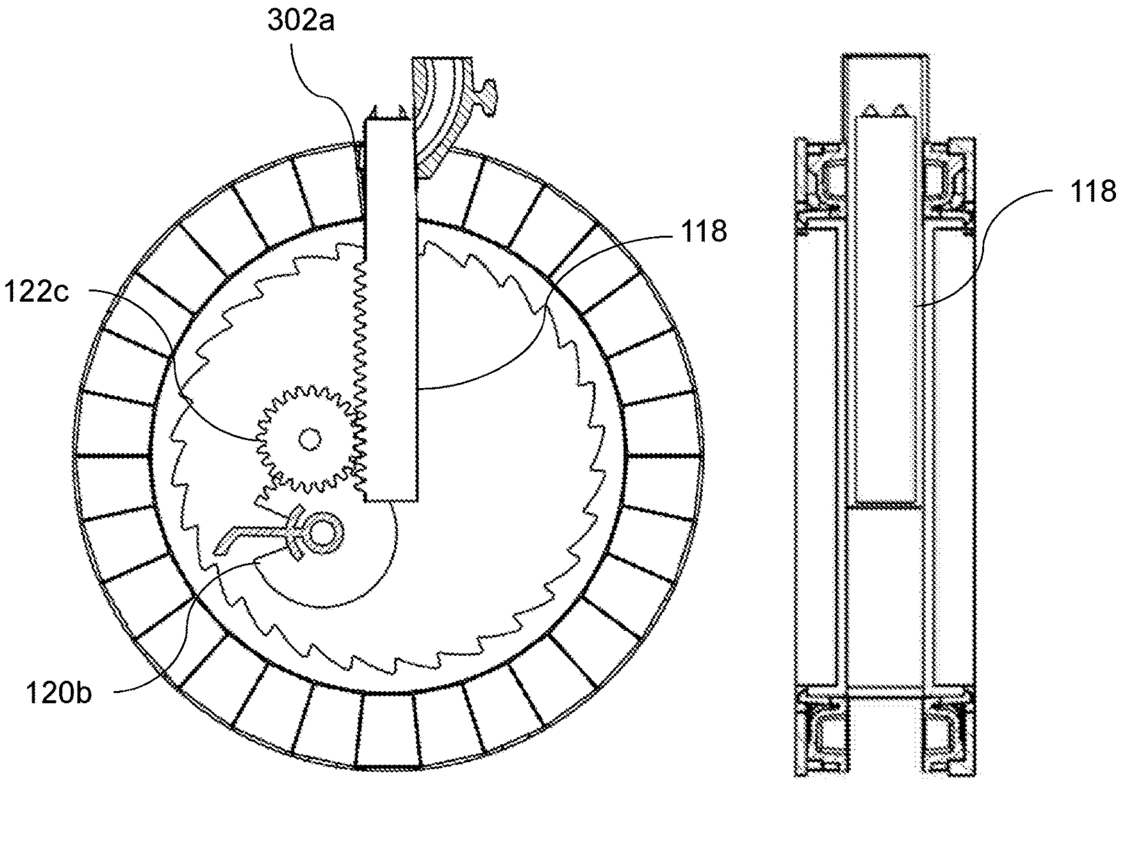

In FIG. 3B, the cover 106 has been rotated such that the gear mechanisms 120, 122 are actuated. As such, the gear wheel 120*b* of the first gear mechanism 120 has been rotated clockwise and in turn the second gear wheel 122*c* of the second gear mechanism 122 is rotated counter-clockwise. The dosing element 118 is thus moved upwards to a position between the inactive position and the dose-administering position. The dosing element 118 penetrates the first pair of medicament cavities 302*a* in this position, removing the seal as will be explained in relation to FIGS. 4A to 4E. In some implementations, the rotation of the cover 106 is between 20° and 85° from the first position when the dosing element 118 is between the inactive position and the dose-administering position.

Figure 3C:
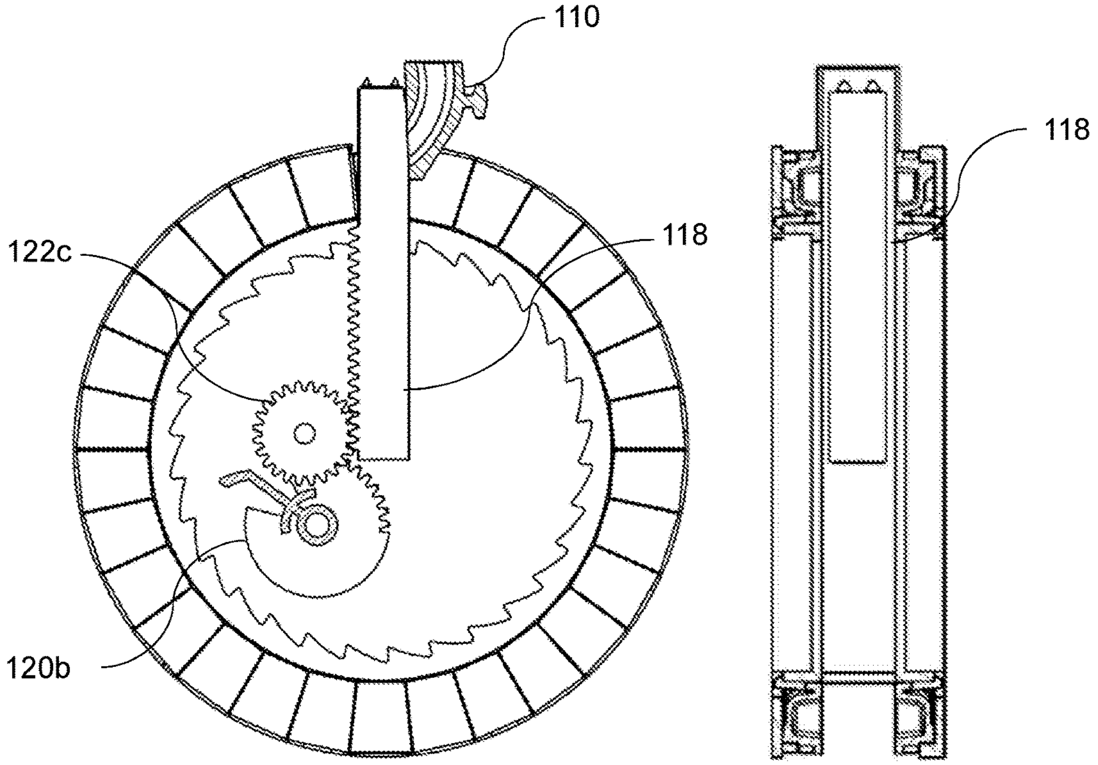

In FIG. 3C, the cover 106 has been rotated into the second position such that the gear wheel 120*b* and the second gear wheel 122*c* are further rotated and the dosing element 118 is moved into the dose-administering position. At least an end of the dosing element 118 has passed through the first pair of medicament cavities 302*a* such that the dosing element 118 is in fluid communication with the duct 110. In this position, a user can inhale medicament from the inhaler, as will be explained in relation to FIGS. 4A to 4E. In some implementations, the rotation of the cover 106 is between 85° and 90° from the first position when the dosing element 118 is in the dose-administering position. This can provide a safety margin for correct operation of the inhaler.

Figure 3D:
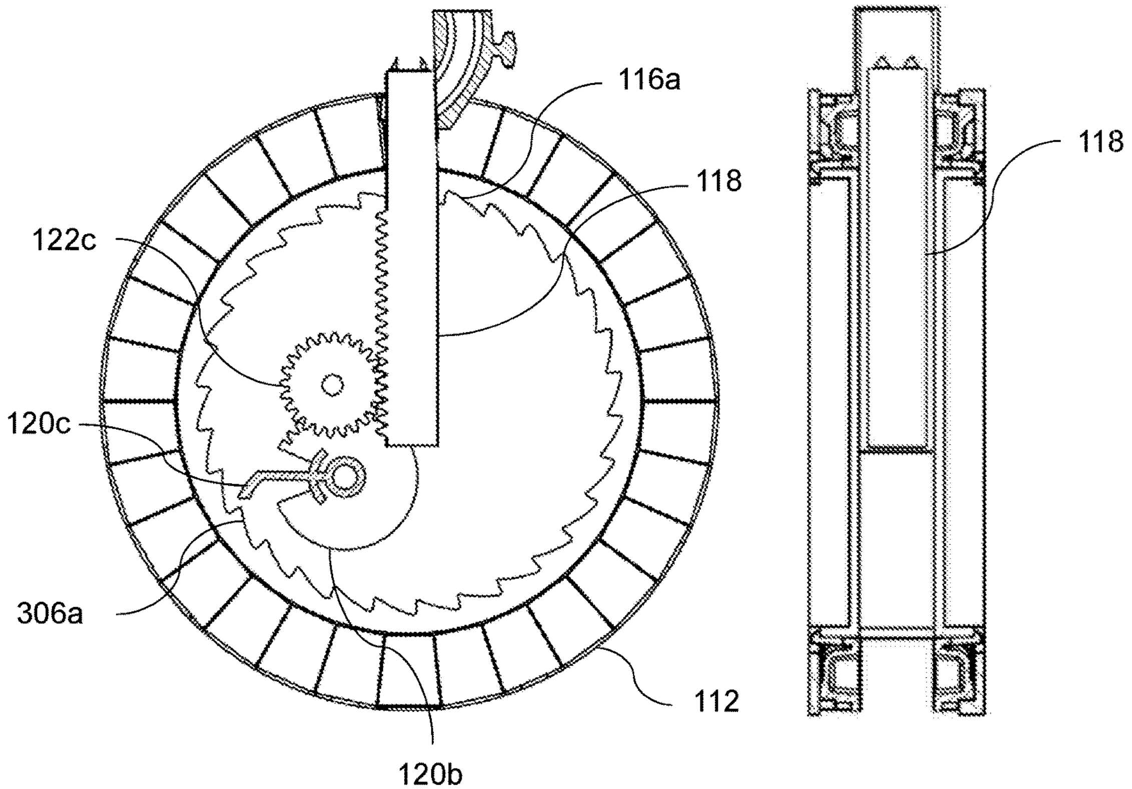

In FIG. 3D, the cover 106 has been rotated away from the second position and back towards the first position such that the gear mechanisms 120, 122 are actuated in the opposite sense to FIGS. 3A to 3C. As such, the gear wheel 120*b* of the first gear mechanism 120 has been rotated counter-clockwise such that the second gear wheel 122*c* of the second gear mechanism 122 is rotated clockwise and the dosing element 118 is moved back to a position between the inactive position and the dose-administering position. The tab 120*c* of the first gear mechanism 120 begins to interact with a corresponding tooth 306*a* of the bracket 116*a* as the rotation of the gear mechanisms 120, 122 continues (it will be appreciated that the tab also begins to interact with a corresponding tooth of the bracket 116*b*, which is not shown). This causes rotation of the brackets 116*a-b* from the first dose delivery position towards a second dose delivery position. In some implementations, the rotation of the cover 106 is between 90° and 20° from the first position when the dosing element 118 is between the inactive position and the dose-administering position.

Figure 3E:
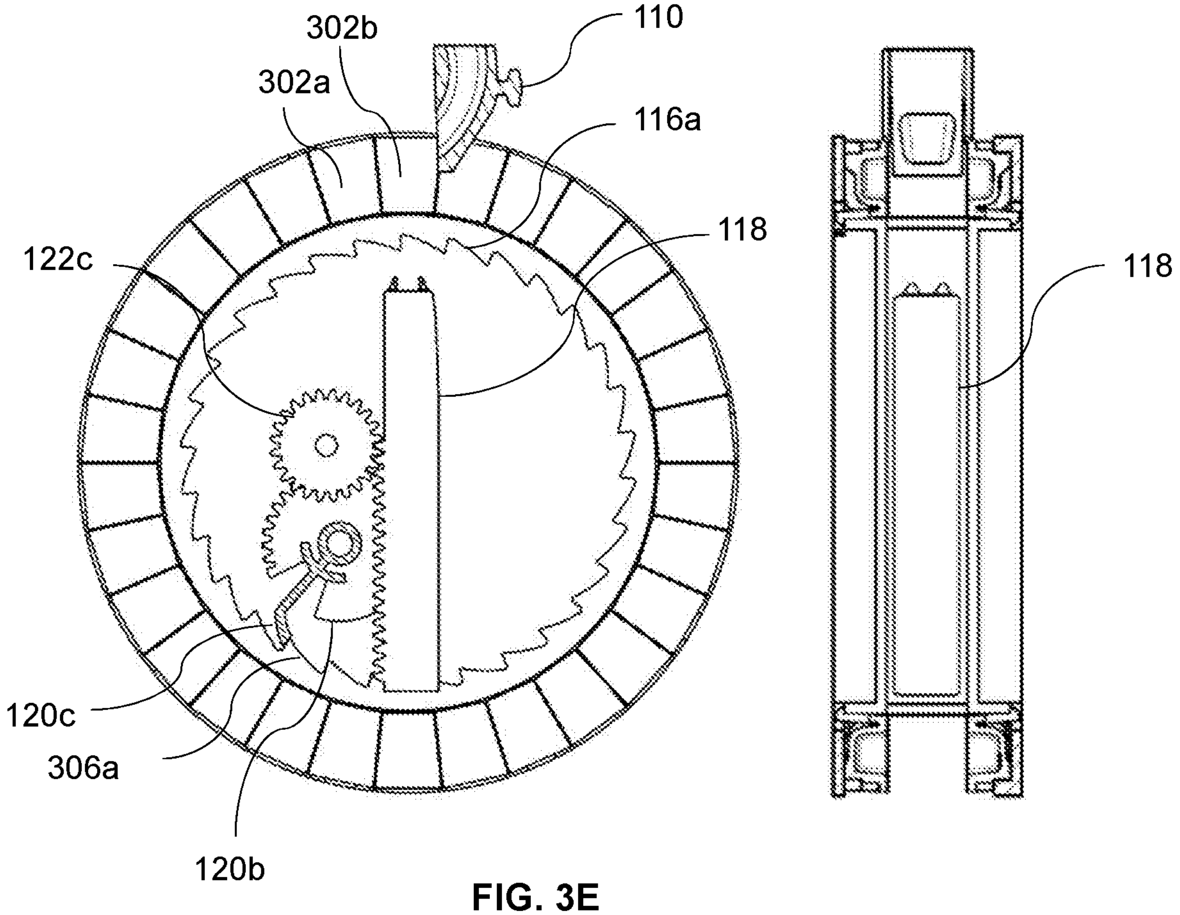

In FIG. 3E, the cover 106 has been returned to the first position and the gear wheel 120*b* and the second gear wheel 122*c* are further rotated such that the dosing element 118 is moved back into the inactive position. The interaction between the tab 120*c* and the teeth of the brackets 116*a-b* has caused rotation of the brackets 116*a-b* in a counter-clockwise direction into the second dose delivery position, as can be seen from the new position of the tooth 306*a* of the brackets 116*a*. A second pair of medicament cavities 302*b*, adjacent the first pair of medicament cavities 302*a*, is now aligned with the dosing element 118. In some implementations, the rotation of the cover 106 is between 20° and 0° from the first position when the dosing element 118 is in the inactive position and brackets 116*a-b* are actuated to move the second pair of medicament cavities 302*b* into the second dose delivery position. The dosing mechanism is now ready to be actuated again for the user to inhale a new dose from the second pair of medicament cavities 302*b*. As such, the dosing mechanism enables both rotation of the dose wheel 112 and movement of the dosing element 118 in a single action of the cover 106.

FIGS. 4A to 4E show the dosing element 118 schematically in cross-section. In particular, FIGS. 4A to 4E show how the dosing element 118 interacts with the medicament cavities to remove the seal and provide fluid communication between at least one of the medicament cavities and the outlet of the mouthpiece 104. As shown in FIGS. 4A to 4E, the dosing element 118 comprises a manifold 400 comprising a number of channels arranged to provide fluid communication between at least one of the medicament cavities and the outlet of the mouthpiece 104 when the dosing element 118 is in the dose-administering position. The manifold 400 enables air to be drawn from the inlets 108*a-b* and through the dosing element 118, where dry powder medicament is entrained and provided to the user at the outlet of the mouthpiece 104. In FIGS. 4A to 4E, the dotted lines represent open boundaries of a particular feature, and do not represent any physical element.

Figure 4A:
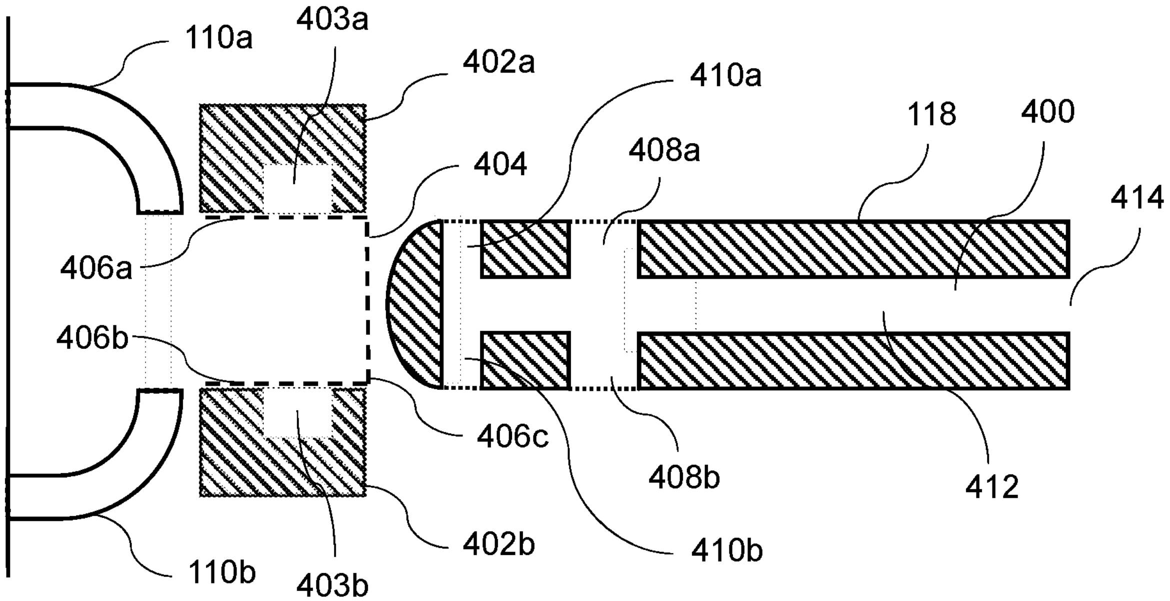
FIGS. 4A to 4E schematically show a dosing element moving from an inactive position to a dose-administering position.

FIG. 4A schematically shows the dosing element 118 in an inactive position. A pair of medicament cavities 402*a-b* is arranged on the dose wheel 112 as discussed above. Each medicament cavity 402*a-b* comprises a volume 403*a-b* for receiving and/or storing a dry powder medicament. The medicament cavities 402*a-b* may be arranged such that the volumes 403*a-b* are inwardly facing, i.e. the open sides of the volumes of the two medicament cavities 402*a-b* face each other. The structure of the medicament cavities 402*a-b* will be described in more detail in in relation to FIGS. 5 to 8. The medicament cavities 402*a-b* may both contain the same medicament or may contain different respective medicaments. In some implementations, one of the two cavities 402*a-b* may be empty, or not present at all. As such, the inhaler 100 is able to provide either single-drug or double-drug delivery in a single dose.

The volumes 403*a-b* hold dry powder medicament and are sealed by a sealing element 404, indicated by the dashed line, to provide the sealed medicament cavities 402*a-b*. The sealing element may be a film or foil, for example an aluminium foil. This sealing element 404 may comprise a first portion 406*a* sealing a first medicament volume 403*a*, a second portion 406*b* sealing a second medicament volume 403*b*, and a third portion 406*c* spanning a gap between the medicament cavities 402*a-b*.

The dosing element 118 comprises at least one first conduit 408*a-b*, at least one second conduit 410*a-b* and at least one third conduit 412. In the inactive position, there is no fluid communication between the dosing element 118 and a pair of ducts 110*a-b* that lead to the mouthpiece 104 of the inhaler 100. Whilst two first conduits 408*a-b*, two second conduits 410*a-b*, one third conduit 412 and two ducts 110*a-b* are shown in FIGS. 4A to 4E, it will be appreciated that different numbers and configurations of conduits could be implemented, as will be explained in relation to FIGS. 9A to 9I.

The first conduits 408*a-b* and the second conduits 410*a-b* are in fluid communication with each other. The third conduit 412 is in fluid communication with at least the first conduits 408*a-b*. The third conduit 412 has an open end 414 that is in fluid communication with the inlets 108*a-b* (not shown). In some implementations, the third conduit 412 is in fluid communication with the inlets 108*a-b* via the internal volume of the housing 102. That is to say, there is no specific structural element inside the housing 102 that connects the inlets 108*a*-b to the third conduit 412. In other implementations, a channel may be provided that connects the inlets 108*a-b* directly to the open end 414 of the third conduit 412.

Figure 4B:
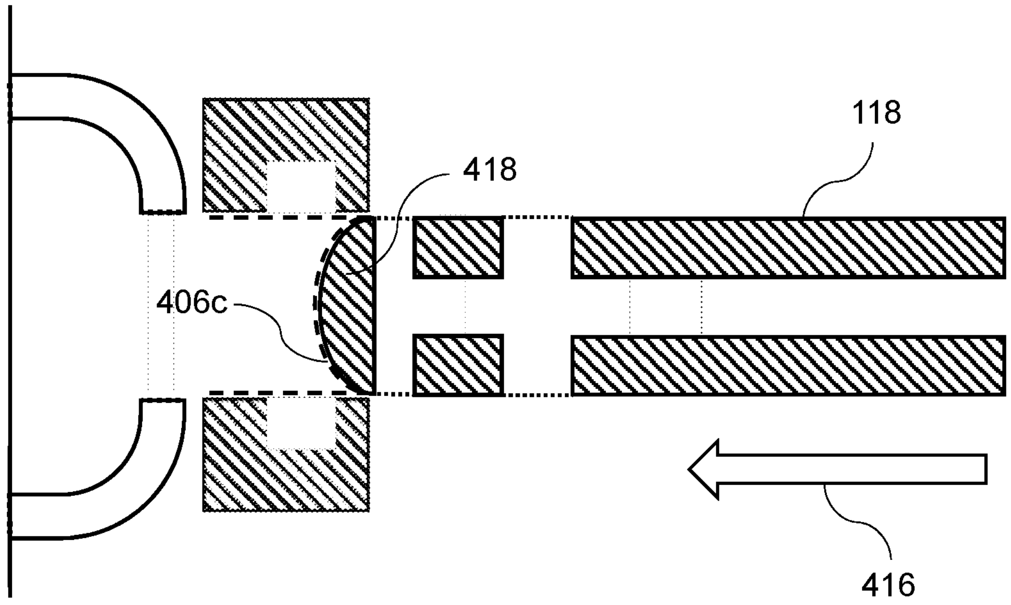

FIG. 4B shows the dosing element 118 at a first position between the inactive position and a dose-administering position. The dosing element 118 is actuated in the direction of arrow 416, for example by the second gear mechanism 122, as discussed above. In this position, a front part 418 of the dosing element makes contact with the third portion 406*c* of the sealing element 404.

Figure 4C:
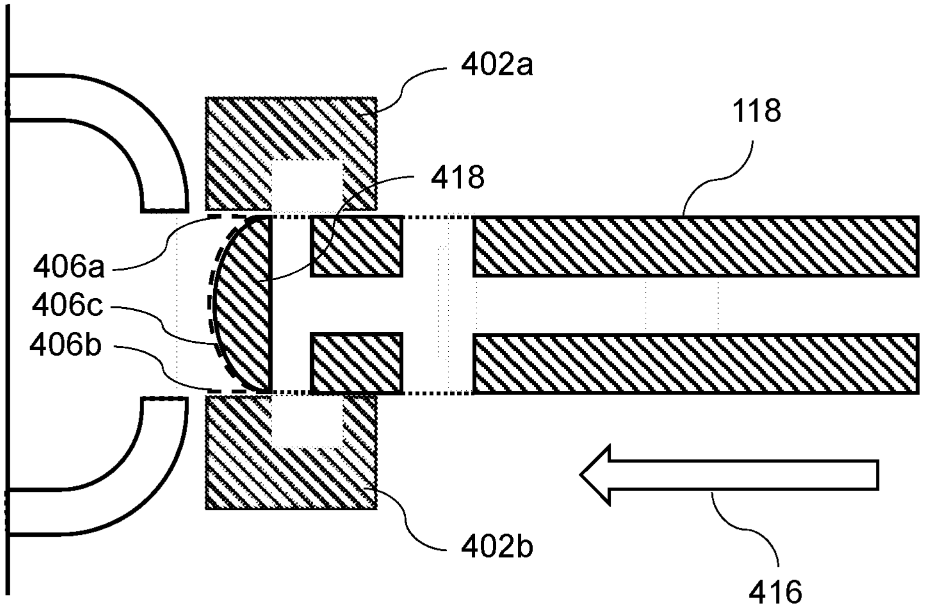

FIG. 4C shows the dosing element 118 at a second position between the inactive position and a dose-administering position. The dosing element 118 continues to be actuated in the direction of arrow 416, for example by the second gear mechanism 122. In this position, the front part 418 of the dosing element pushes sealing element 404 in the direction of arrow 416 such that the first and second portions 406*a-b* begin to be peeled away from their respective medicament cavities 402*a-b*.

Figure 4D:
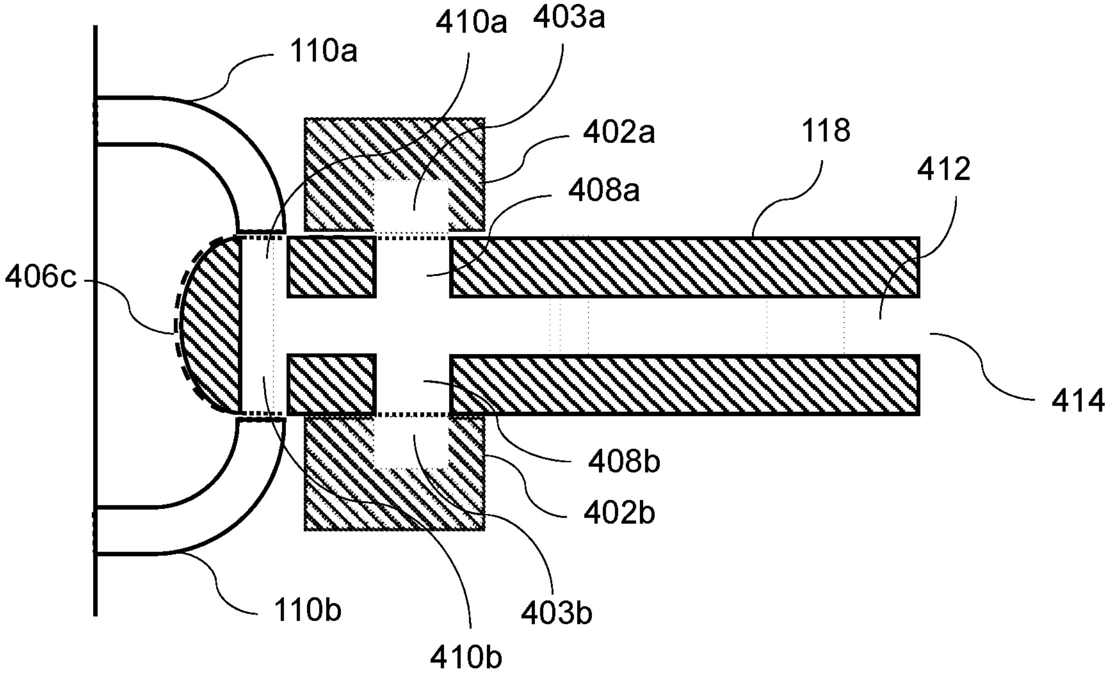

FIG. 4D shows the dosing element 118 in the dose-administering position. In this position, the first and second portions 406*a-b* have been peeled away from their respective medicament cavities 402*a-b* such that the volumes 403*a-b* of the medicament cavities 402*a-b* are at least partially open. The first conduits 408*a-b* are aligned with respective medicament cavities 402*a-b*, such that the first conduits 408*a-b* are in fluid communication with their respective medicament cavities 402*a-b*. Furthermore, the second conduits 410*a-b* are aligned with the ducts 110*a-b* that lead to the mouthpiece 104 of the inhaler 100, such that the second conduits 410*a-b* are in fluid communication with the outlet of the mouthpiece 104. As the third conduit 412 is in fluid communication with the inlets 108*a-b* and the first conduits 408*a-b*, the first conduits 408*a-b* are in fluid communication with the second conduits 410*a-b* and the second conduits 410*a-b* are in fluid communication with the ducts 110*a-b*, a fluid path is provided between the inlets 108*a-b*, the volumes 403*a-b* of the medicament cavities 402*a-b*, and the outlet of the mouthpiece 104.

Figure 4E:
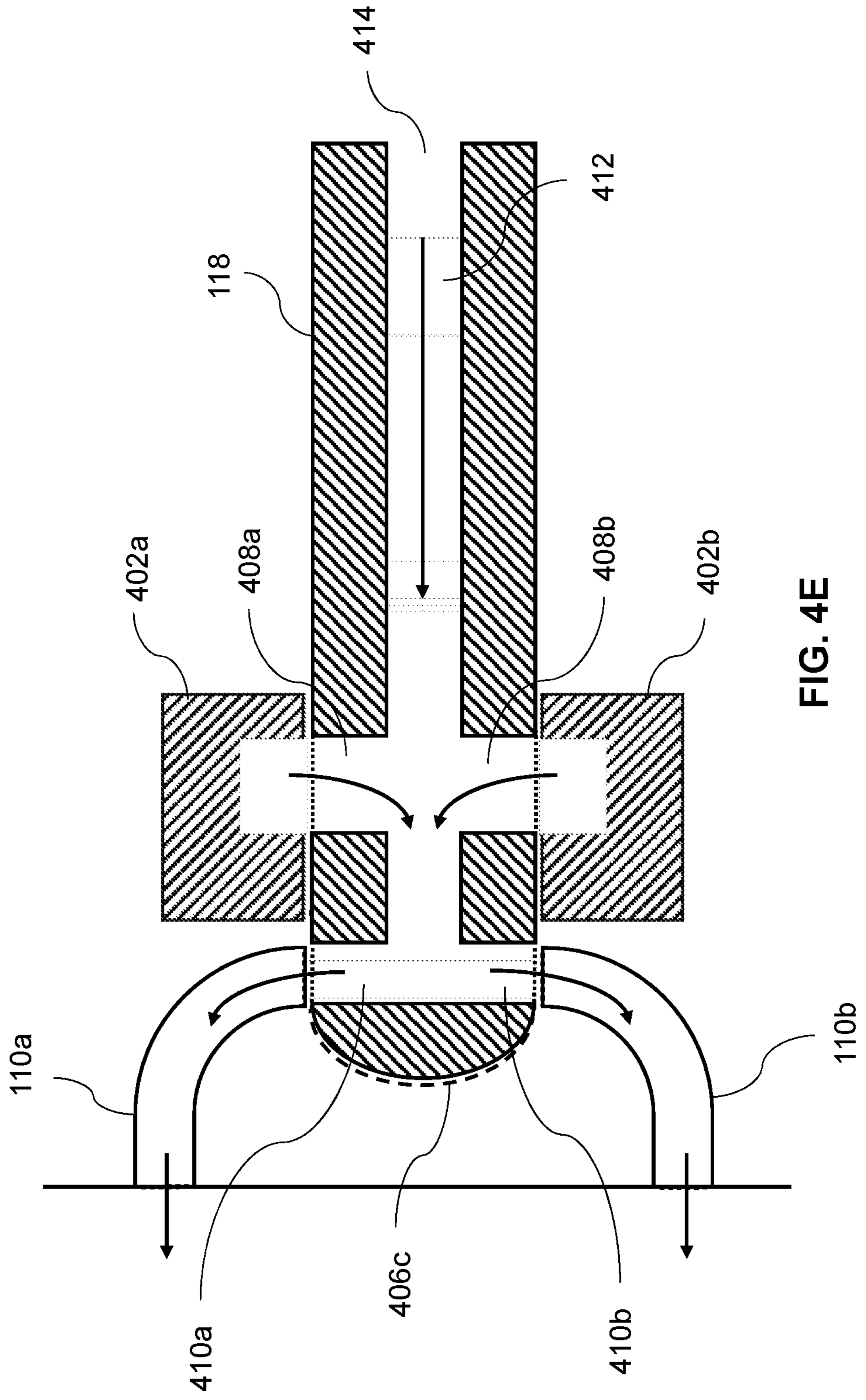

The fluid communication provided by the dosing element 118 in the dose-administering position is shown in FIG. 4E. During an inhalation by the user, a pressure difference across the dosing element 118 draws air from the inlets 108*a-b* into the third conduit 412. This air passes into and through the first conduits 408*a-b*, thus entraining dry powder medicament from the medicament cavities 402*a-b*. Dry powder medicament from each cavity 402*a-b* is then mixed in the areas between and downstream of the first conduits 408*a-b*. The air, now including the mixed dry powder medicament, is then passed into the second conduits 410*a-b* and to the ducts 110*a-b*. The air and mixed dry powder medicament are then inhaled by the user through the outlet of the mouthpiece 104.

The dry powder inhalers disclosed herein provide a dosing mechanism having a dose wheel 112 and a dosing element 118 that allow two medicament cavities 402*a-b* to be simultaneously accessed for delivery in a combined dose. The dosing element 118 acts both as a mechanism for accessing the medicament cavities 402*a-b* and delivering the medicament to the user. This allows medicaments from two separate cavities to be deaggregated and mixed properly before inhalation by a user. The mechanism allows such doses to be delivered in a repeatable manner, as the dosing mechanism enables both rotation of the dose wheel 112 and movement of the dosing element 118 in a single action of the cover 106. The mechanism has a simpler construction than those currently known for provided combined doses of multiple medicaments.

Figure 5:
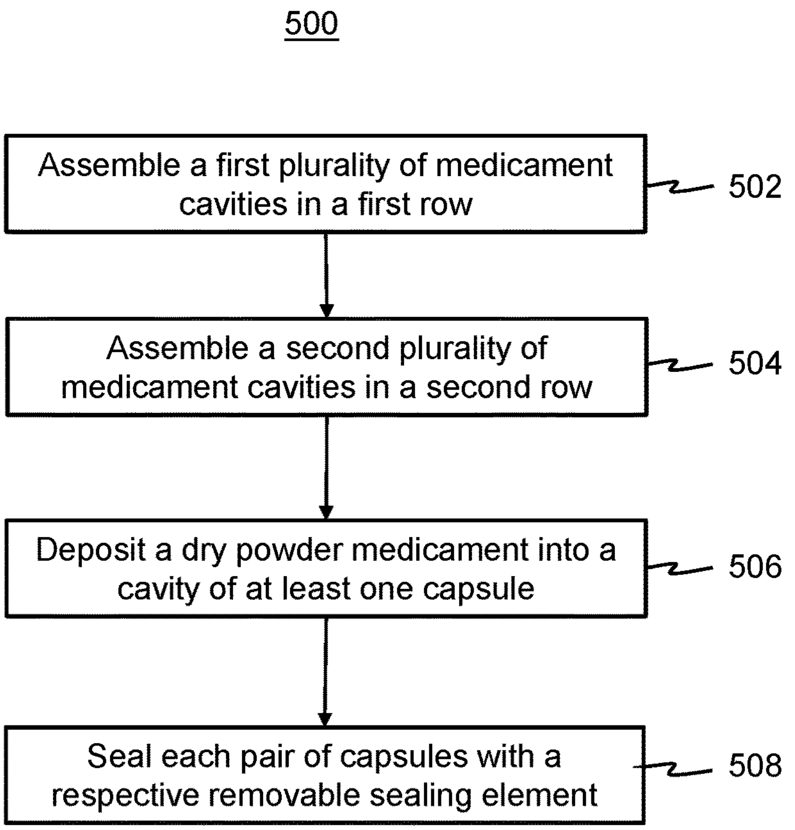
FIG. 5 is a flow diagram showing a method of packaging a dry powder medicament.
Figure 6A:
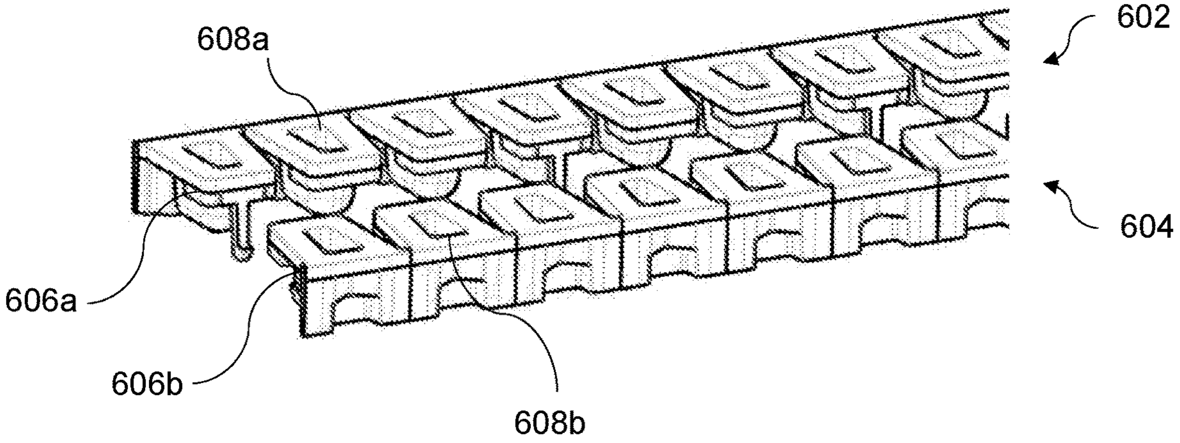
FIGS. 6A to 6C show different stages of a method of packaging a dry powder medicament.
Figure 6B:
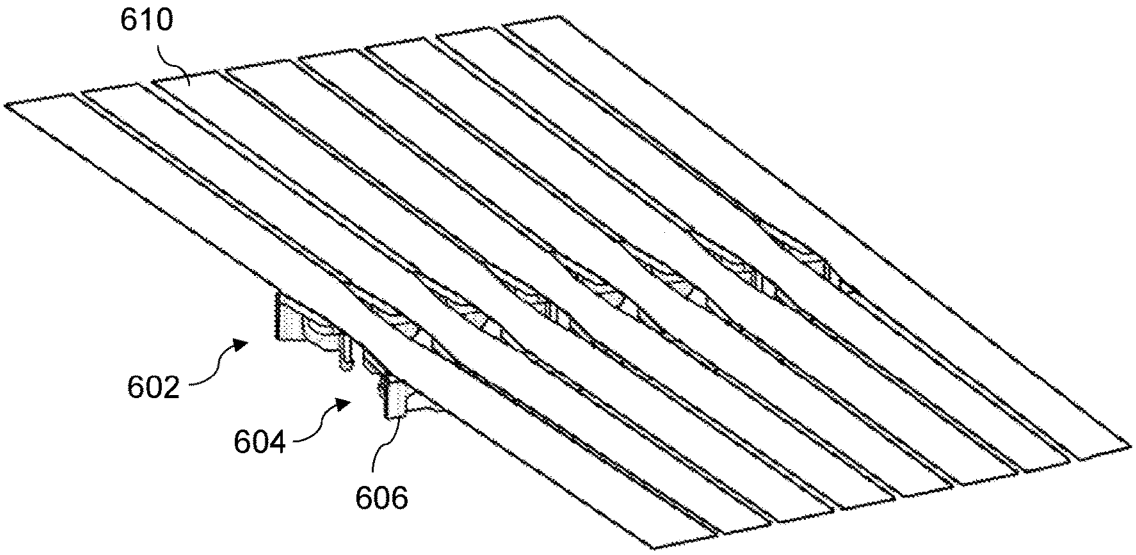
Figure 6C:
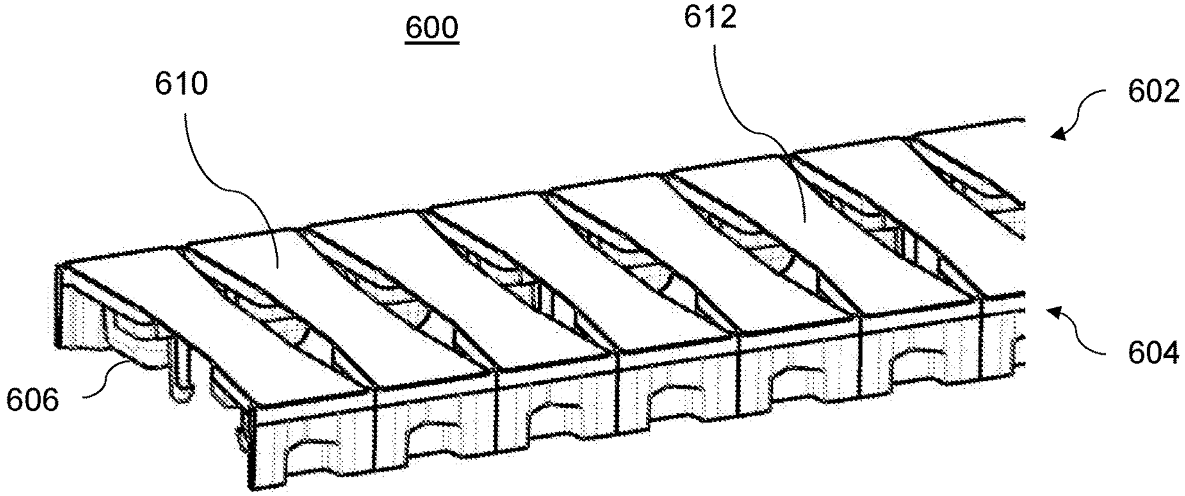

FIG. 5 is a flow diagram showing a method 500 of packaging dry powder medicament. FIGS. 6A to 6C show the packaging at different stages of the process. The packaging may be used in a dry powder inhaler as discussed above.

At step 502, a first plurality of medicament cavities is assembled in a first row. Each medicament cavity in the first row may comprise a volume for containing dry powder medicament. Each medicament cavity in the first row may be a medicament cavity 402*a*, and each volume may be a volume 403*a*, as discussed in relation to FIGS. 4A to 4E. In some implementations, the plurality of medicament cavities in the first row are assembled contiguously. That is to say, at least part of a given cavity is in contact with at least part of the next cavity in the row. In such implementations, the cavities may be formed or manufactured as a unitary structure. In other implementations, there may be gaps between successive cavities in the first row, and the cavities may be connected by a suitable connecting element. The cavities in the first row may have a tapered structure so that they can be assembled into an annular form, as will be explained in relation to FIGS. 8A to 8C.

At step 504, a second plurality of medicament cavities is assembled in a second row. The second row is arranged parallel to and spaced from the first row. That is to say, there is a constant distance between the two rows along their length. Each medicament cavity in the second row may comprise a volume for containing dry powder medicament. Each medicament cavity in the first row may be a medicament cavity 402*b*, and each volume may be a volume 403*b*, as discussed in relation to FIGS. 4A to 4E. In some implementations, the plurality of medicament cavities in the second row are assembled contiguously. In such implementations, the cavities may be formed or manufactured as a unitary structure. In other implementations, there may be gaps between successive cavities in the second row, and the cavities may be connected by a suitable connecting element. The cavities in the second row may have a tapered structure so that they can be assembled into an annular form, as will be explained in relation to FIGS. 8A to 8C.

FIG. 6A shows first and second rows of cavities assembled according to steps 502 and 504. As shown in FIG. 6A, a first row 602 comprises a first plurality of cavities 606*a*, each comprising a respective volume 608*a*. A second row 604 comprises a second plurality of cavities 606*b*, each comprising a respective volume 608*b*. The rows are assembled parallel to and spaced from each other. In the implementation of FIG. 6A, the cavities 606 in each row 602, 604 are assembled contiguously. The volumes 608*a-b* are open in order to allow deposition of dry powder medicament into the volumes 608*a-b*.

Each cavity in the first row 602 and a corresponding cavity in the second row 604 form a pair. Each pair may then be delivered to the user as part of the same dose. In some implementations, the number of cavities in the first row 602 is the same as the number of cavities in the second row 604, such that a corresponding number of pairs are formed. Any suitable number of cavities may be present in each row. For example, each row can contain between 10 and 100 cavities. In some implementations, each row contains 30 or 60 cavities.

At step 506, dry powder medicament is deposited into a volume of at least one cavity. In some implementations, dry powder medicament is deposited into a volume of one or more cavities in the first row 602. In some implementations, dry powder medicament is deposited into a volume of one or more cavities in the second row 604. In some implementations, a dry powder medicament is deposited into a volume of all cavities in one or both rows. As discussed above, in some implementations a first medicament may be deposited into one or more cavities of the first row 602 and a second medicament, different to the first medicament, may be deposited into one or more cavities of the second row 604. In this way, two different medicaments that cannot be formulated and/or stored together can be delivered to a user in a single dose. In other implementations, a single medicament may be deposited into one or more cavities of the two rows.

In some implementations, not all cavities are filled with dry powder medicament. For example, some of the cavities in one or both of the rows may be left empty. In another example, at least one of the cavities may be a "dummy" cavity, meaning the cavity structure does not have a volume for containing a medicament. This allows different dosing regimens to be provided. In one implementation, only one row may contain any cavities.

At step 508, each pair of cavities is sealed with a respective removable sealing element. That is to say, a single sealing element is applied to a cavity from the first row and a corresponding cavity from the second row. The sealing elements are attached to a top surface of each cavity in a respective pair such that the respective volumes are covered and sealed cavities are provided. Each sealing element may be a sealing element 404 as discussed in relation to FIGS. 4A to 4E. The sealing element may be a film or foil, for example an aluminium foil. In some implementations, the sealing element is heat sealed to the respective cavities, although other sealing methods known in the art could also be used, such as adhesion, induction sealing, ultrasonic welding and the like. Each removable sealing element is configured to be peeled from the cavities by application of pressure to a portion of the sealing element between the first and second rows, as explained in relation to FIGS. 4A to 4E.

In some implementations, the step of sealing each pair of cavities comprises sealing a strip of sealing material to each pair. The strip of sealing material may be applied to the cavities using any of the techniques discussed above. The strip of sealing material may be longer than the width of the packaging. That is to say, each strip may have a length longer than that distance from the outer side of the first row to the outer side of the second row. FIG. 6B shows an example of sealing elements 610 in the form of strips of sealing material being applied to the cavities in this way. In these implementations, the method then comprises trimming each strip of sealing material to the width of packaging. FIG. 6C shows an example of sealing elements 610 trimmed to the width of the cavities in this way, with a portion 612 of the sealing element 610 spanning the gap between the first and second rows 602, 604 (equivalent to the third portion 406*c* shown in FIGS. 4A to 4E).

As shown in FIG. 6C, the final packaging 600 comprises a first row 602 comprising a first plurality of medicament cavities 606*a*, a second row 604 comprising a second plurality of medicament cavities 606*b* parallel to and spaced from the first row 602. Each cavity 606*a* in the first row and a corresponding cavity 606*b* in the second row form a pair. A dry powder medicament is deposited into a volume of at least one of the cavities 606*a-b*. A plurality of removable sealing elements 610 seal the volumes 608 of respective pairs of cavities 606*a-b*. Each sealing element 610 is configured to be peeled from the cavities 606*a-b* by application of pressure to a portion 612 of the sealing element 610 between the first and second rows 602, 604.

Figure 7:
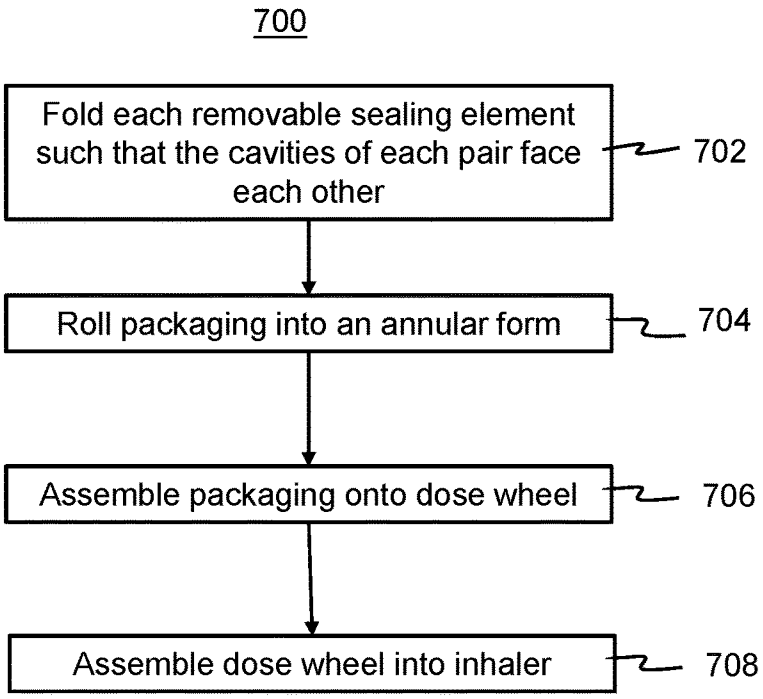
FIG. 7 is a flow diagram showing a method of assembling the packaging in a dry powder inhaler.
Figure 8A:
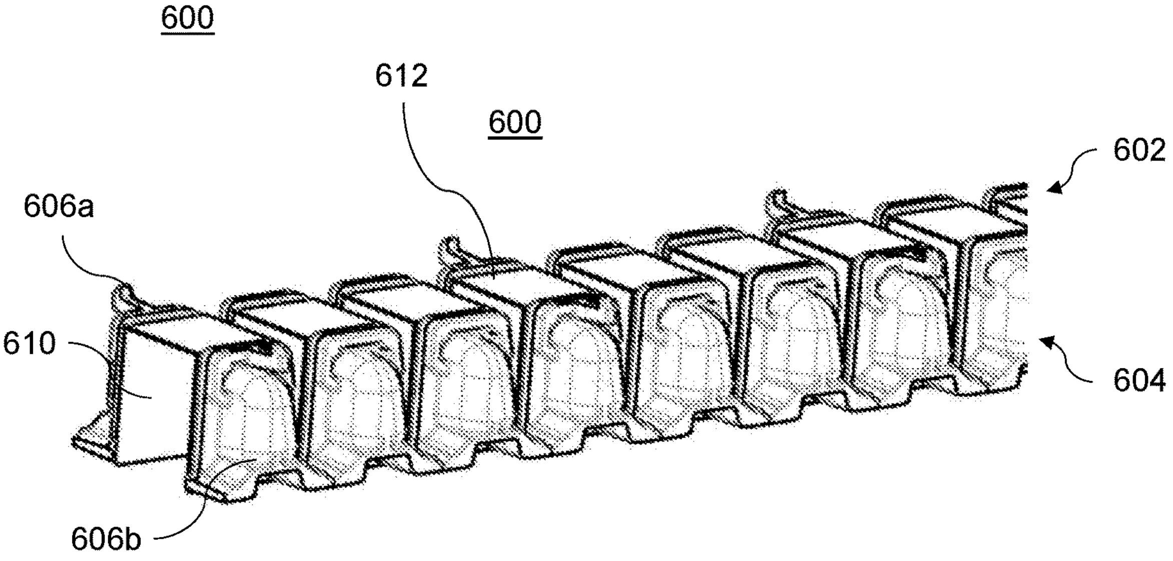
FIGS. 8A to 8D show different stages of assembly of the packaging in the inhaler.
Figure 8B:
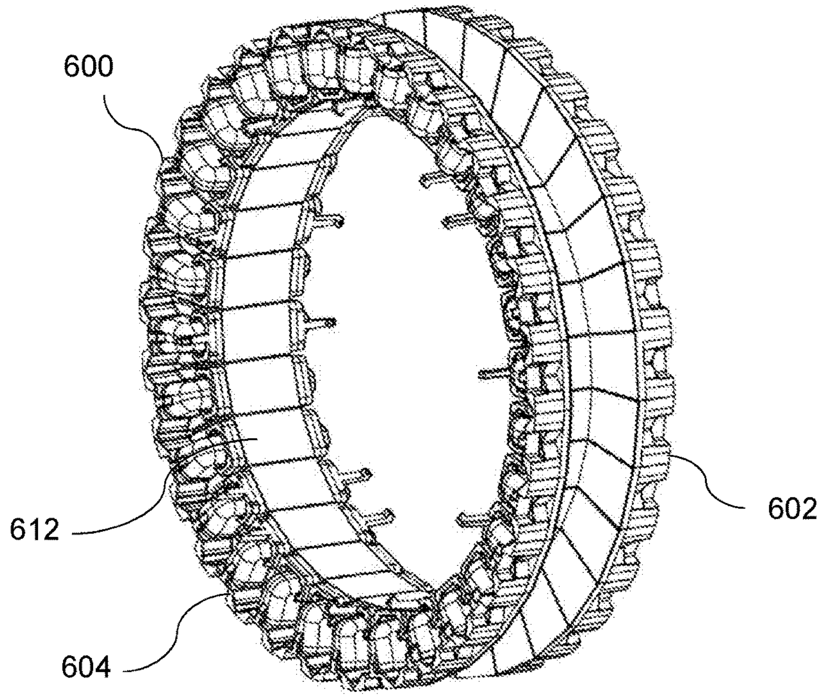
Figure 8C:
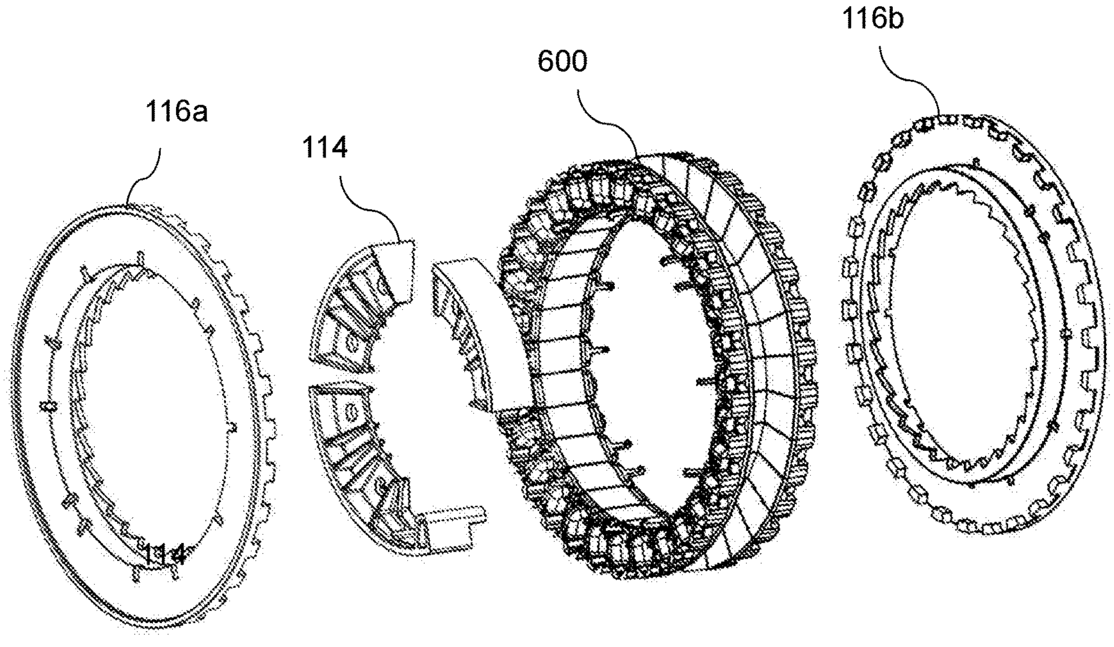

FIG. 7 is a flow diagram showing a method 700 of assembling the packaging 600 in a dry powder inhaler. FIGS. 8A to 8C show the packaging at different stages of the assembly process.

At step 702, each removable sealing element is folded such that the volumes of each cavity in a respective pair face each other. FIG. 8A shows the cavities 606*a-b* arranged at 90° angle to their position in FIG. 6C. The cavities 606*a-b* are folded inwardly, such that the top surfaces of each cavity in a respective pair face each other. One side of the portion 612 of the sealing element 610 between the first and second rows is exposed to receive a dosing element 118 of an inhaler. It is noted that the packaging 600 is shown in FIG. 8A flipped from its orientation in FIG. 6C.

At step 704, the packaging 600 is rolled into an annular form for assembly onto a dose wheel 112 of an inhaler. FIG. 8B shows the rolled packaging 600 before it is assembled in the inhaler. The side of each portion 612 of the sealing elements 610 spanning the gap between the first and second rows 602, 604 that is exposed to receive a dosing element 118 faces inwards for interaction with the dosing element 118.

At step 706, the packaging 600 is assembled onto the dose wheel 112 of the inhaler. In particular, the packaging may be assembled onto the base 114 such that the base 114 holds the cavities at a fixed distance from each other in the annular form. The brackets 116*a-b* are then attached to the packaging 600 from each side. The brackets 116*a-b* may be attached to the packaging 600 by any suitable means, for example by a clip mechanism or a snap fit. FIG. 8C shows parts of the dose wheel 112 and the packaging 600 before they are assembled.

Figure 8D:
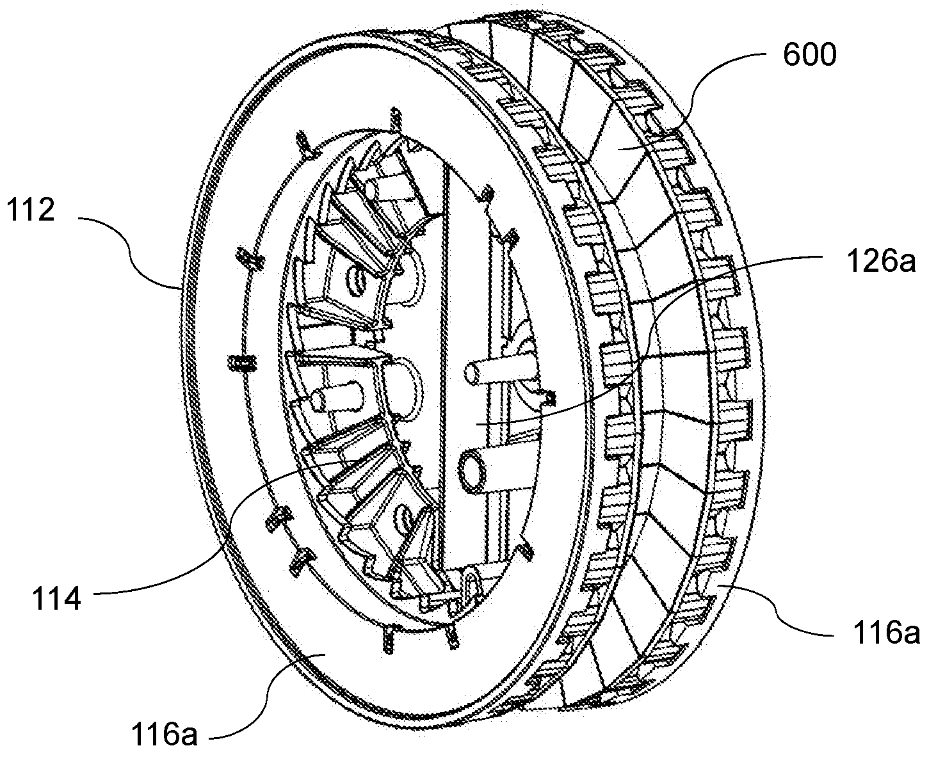

At step 708, the assembled dose wheel 112 is installed in the inhaler. This can include attaching the dose wheel 112 to the plates 126*a-b*. FIG. 8D shows the dose wheel 112 installed with the first plate 126. As shown, the base 114 comprises holes for receiving shafts for the gear mechanisms 120, 122. As discussed above, the dose wheel 112 is rotatable relative to a dosing element 118 of the inhaler 100 between a plurality of dose delivery positions. This allows different pairs of cavities 606*a-b* in the packaging 600 to be accessible to the dosing element 118 in each of the dose delivery positions.

As discussed above, when the packaging is assembled on the dose wheel 112, at least one pair of cavities 606*a-b* may be in a dose delivery position. The dosing element 118 may move from the inactive position inside the dose wheel 112 to a dose-administering position. As described in relation to FIGS. 4A to 4E, the dosing element 118 peels the removable sealing element 610 from the pair of cavities 606*a-b* that are in the dose delivery position such that, when the dosing element 118 is in the dose-administering position, fluid communication is provided between the volumes 608*a-b* of the cavities 606*a-b* in the dose delivery position and the outlet of the inhaler 100. The dosing element 118 may then return to the inactive position and the dose wheel 112 may be rotated to the next dose delivery position ready for administration of the next dose.

The methods of packaging dry powder medicaments disclosed herein, and the packaging produced by such methods, provide for filling a number of volumes in a linear row, before being assembled into an inhaler. This allows multiple cavities to be easily filled and sealed such that they can be provided in a combined dose.

FIGS. 9A to 9I schematically show alternative arrangements of the dosing element 118. The dosing elements 118 shown in FIGS. 9A to 9I have different numbers and configurations of conduits from the dosing element 118 shown in FIGS. 4A to 4E, but are still able to provide fluid communication between at least one medicament cavity and the outlet of a mouthpiece when in a dose-administering position. In FIGS. 9A to 9I, dotted lines represent open boundaries of a particular feature, and do not represent any physical element.

Figure 9A:
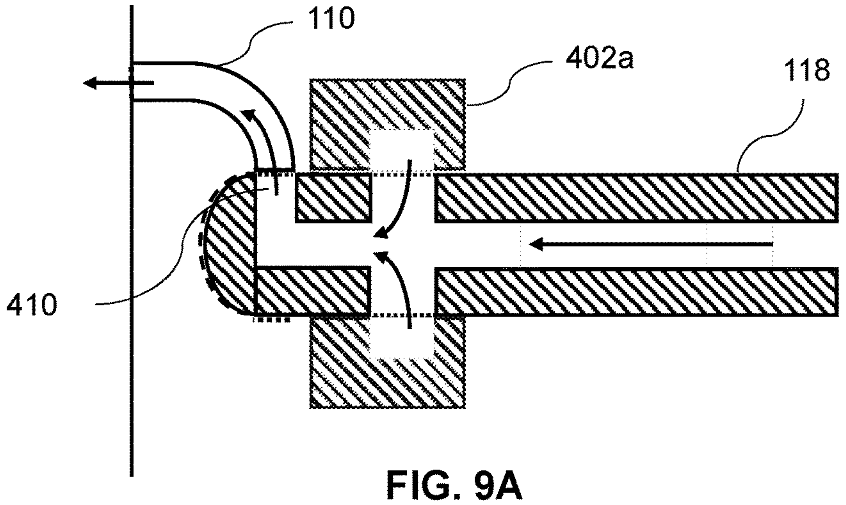
FIGS. 9A to 9I show alternative configurations for a dosing element.

FIG. 9A schematically shows a dosing element 118 similar to that shown in FIGS. 4A to 4E. However, only a single second conduit 410 and corresponding duct 110 are present, instead of two. Therefore, the dry powder medicament from both medicament cavities 402*a-b* follows the same path to the outlet of the inhaler. Whilst the second conduit 410 and the duct 110 are shown on the same side of the dosing element 118 as the first medicament cavity 402*a*, it will be appreciated that they could be present at any suitable position on the dosing element 118 to provide fluid communication to the outlet. This arrangement can provide a simpler structure for a dosing element 118 and an inhaler as a whole, as only a single path to the outlet is provided.

Figure 9B:
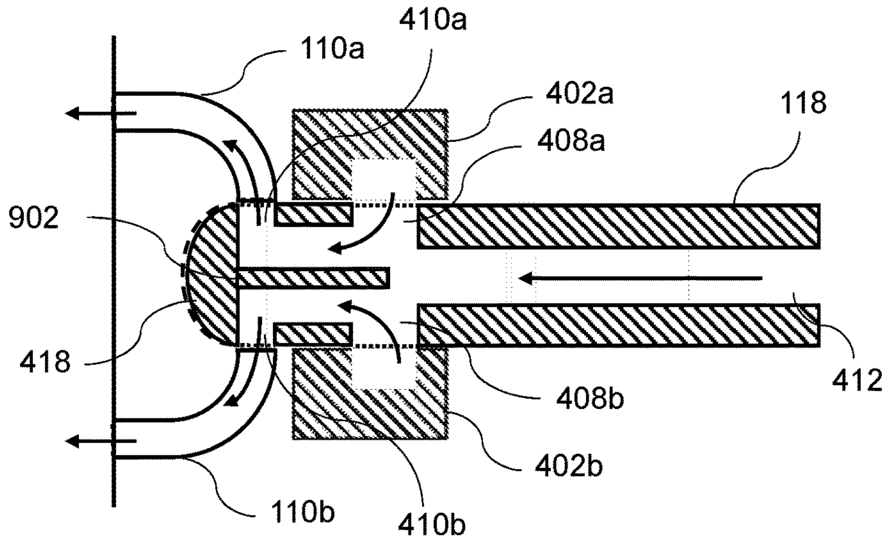

FIG. 9B schematically shows a dosing element 118 similar to that shown in FIGS. 4A to 4E. However, a divider 902 is attached to the front part 418 of the dosing element 118. The divider 902 serves to isolate the first conduit 408*a* and the second conduit 410*a* from the first conduit 408*b* and the second conduit 410*b*. That is to say, each medicament cavity 402*a-b* has its own respective path to the outlet of the inhaler. This arrangement would reduce mixing of the medicaments in each medicament cavity 402*a-b* before they reach the outlet.

Figure 9C:
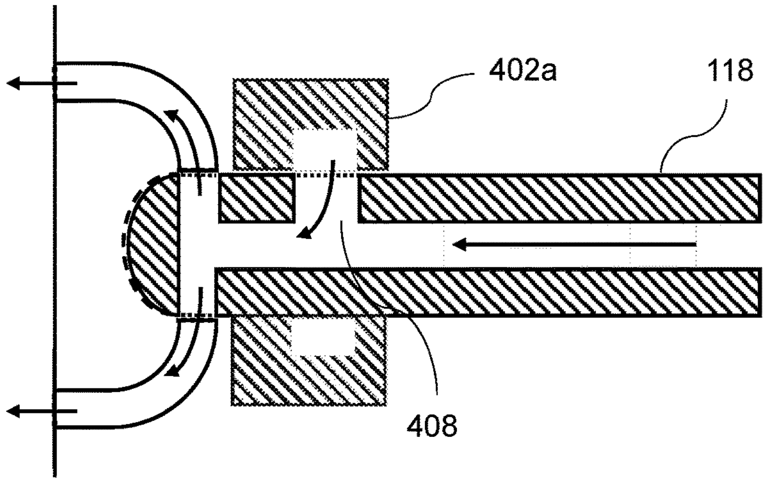

FIG. 9C schematically shows a dosing element 118 similar to that shown in FIGS. 4A to 4E. However, only a single first conduit 408 is present, instead of two. Therefore, only dry powder medicament from a single cavity is provided to the outlet. It will be appreciated that a similar effect could be provided with a dosing element 118 the same as shown in FIGS. 4A to 4E, by having only a single medicament cavity in a dose delivery position (or a single row of medicament cavities), or filling only a single medicament cavity in a pair with dry powder medicament.

Figure 9D:
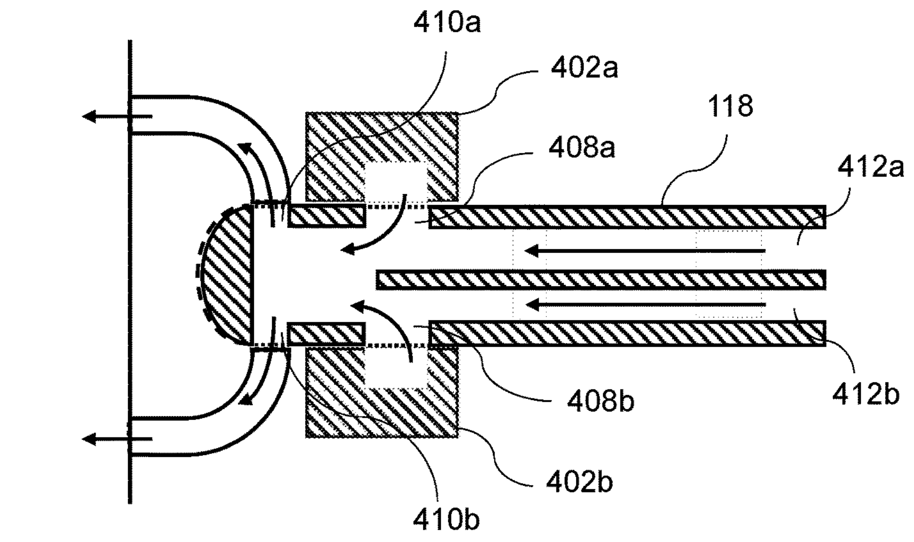

FIG. 9D schematically shows a dosing element 118 similar to that shown in FIGS. 4A to 4E. However, two third conduits 412*a-b* are provided instead of one. Each third conduit 412*a-b* is in fluid communication with a respective first conduit 408*a-b*. The first conduits 408*a-b* are each in fluid communication with the second conduits 410*a-b*. Each third conduit 412*a-b* may be in fluid communication with a respective inlet 108*a-b*, or the third conduits 412*a-b* may be in fluid communication with the same inlet. This can provide an alternative flow regime for entraining medicament from the cavities 402*a-b*.

Figure 9E:
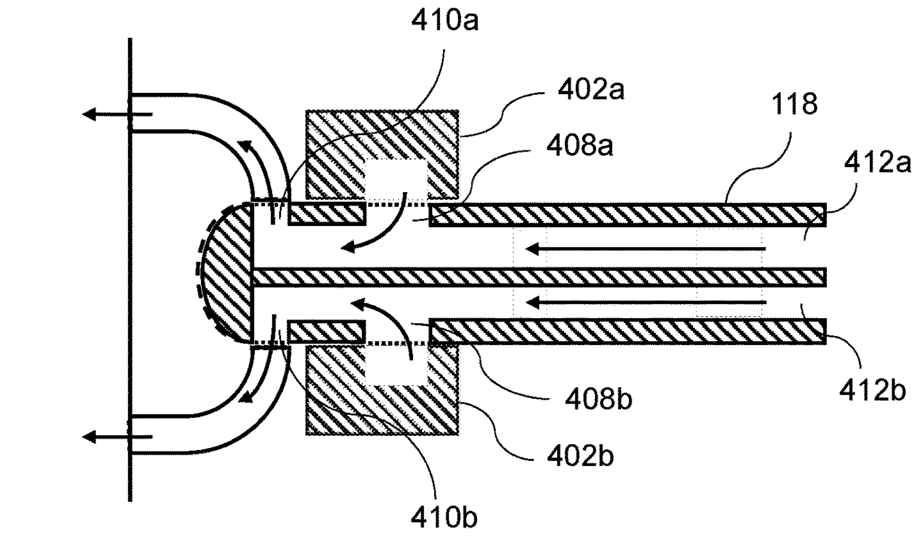

FIG. 9E schematically shows a dosing element 118 similar to that shown in FIG. 9D. However, the two third conduits 412*a-b* are in fluid communication with a respective first conduit 408*a-b* and a respective second conduit 410*a-b*. That is to say, two separate flow paths are provided in the dosing element 118, wherein each medicament cavity 402*a-b* has its own respective path. This arrangement would prevent mixing of the medicaments in each medicament cavity 402*a-b* before they reach the outlet.

Figure 9F:
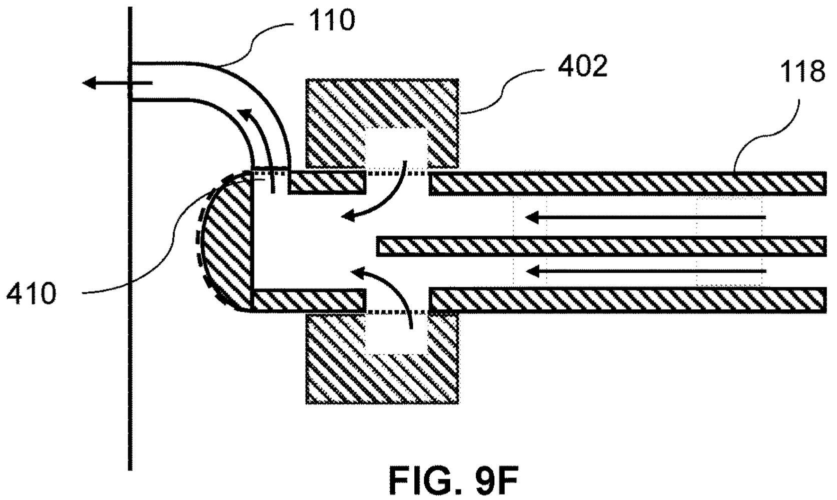

FIG. 9F schematically shows a dosing element 118 similar to that shown in FIG. 9D. However, only a single second conduit 410 and corresponding duct 110 are present. Therefore, the dry powder medicament from both medicament cavities 402*a-b* follows the same path to the outlet of the inhaler. Whilst the second conduit 410 and the duct 110 are shown on the same side of the dosing element 118 as the first medicament cavity 402*a*, it will be appreciated that they could be present at any suitable position on the dosing element 118 to provide fluid communication to the outlet. This provides a combination of an alternative flow regime for entraining medicament from the cavities and a simpler structure.

Figure 9G:
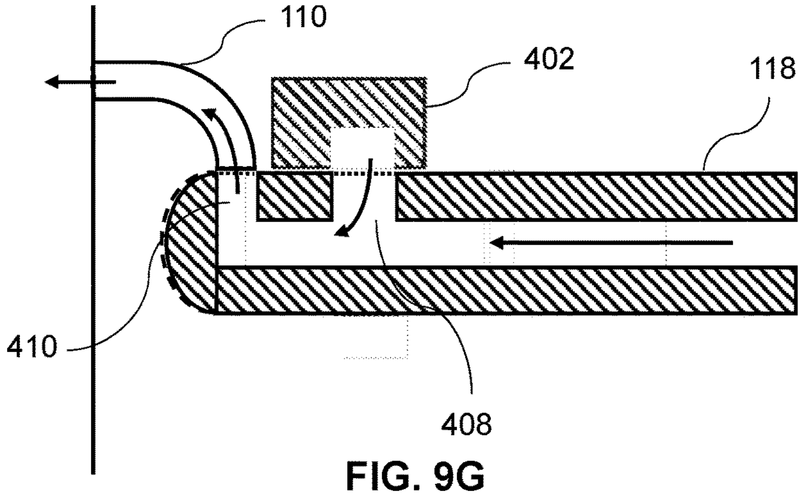

FIG. 9G schematically shows a dosing element 118 similar to that shown in FIGS. 9A and 9C. However, only a single second conduit 410 and corresponding duct 110, and only a single first conduit 408 and corresponding medicament cavity 402 are present. Therefore, dry powder medicament from a single cavity is provided to the outlet via a single path. This provides a simple structure for implementations where only a single type of medicament is required.

Figure 9H:
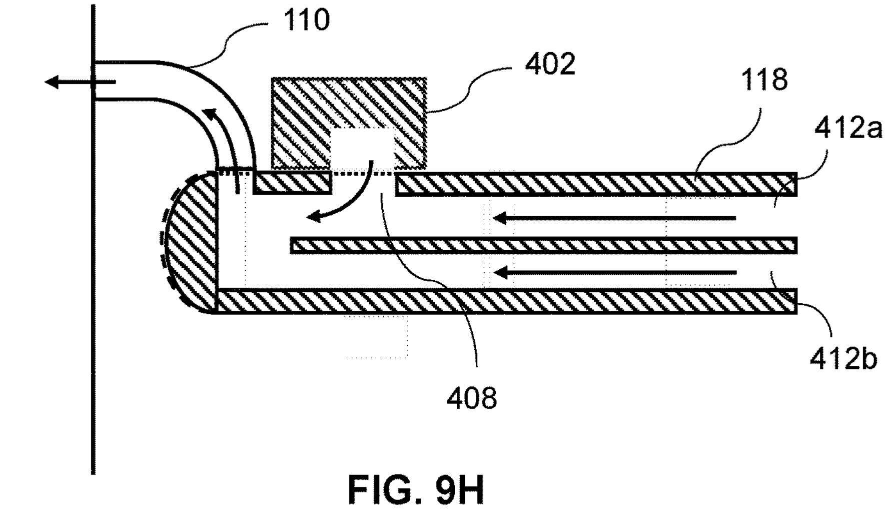

FIG. 9H schematically shows a dosing element 118 similar to that shown in FIG. 9G. However, two third conduits 412*a-b* are provided. Each third conduit 412*a-b* is in fluid communication with the first conduit 408. As such, air from one third conduit 412*a* is used to entrain dry powder medicament from the medicament cavity 402, and air from each of the third conduits 412*a-b* is used to transport the dry powder medicament to the outlet via a single path. This provides a simple structure and alternative flow regime for implementations where only a single type of medicament is required.

Figure 9I:
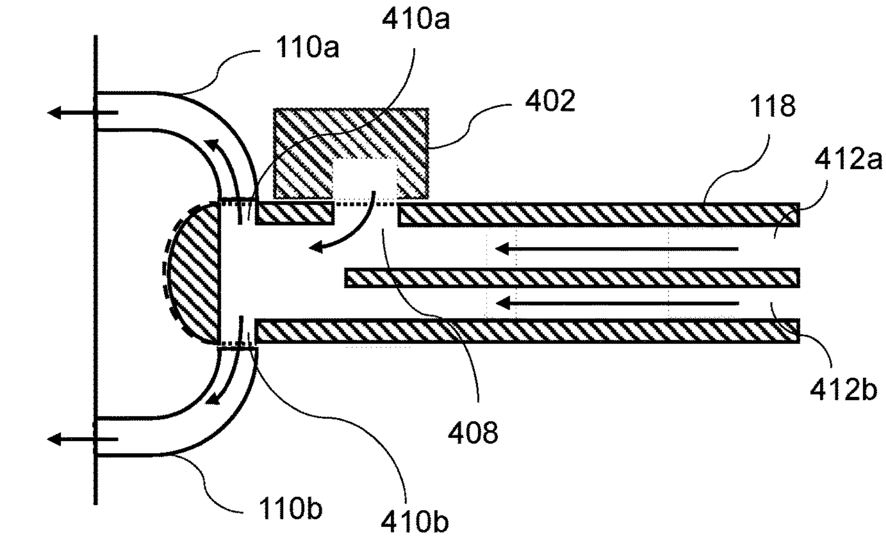

FIG. 9I schematically shows a dosing element 118 similar to that shown in FIG. 9H. However, two first conduits 410*a-b* and corresponding ducts 110*a-b* are provided. Therefore, air from the first conduit 412*a* is used to entrain dry powder medicament from the medicament cavity 402, and air from each of the third conduits 412*a-b* is used to transport the dry powder medicament to the outlet via two flow paths. This provides an alternative flow regime for implementations where only a single type of medicament is required.

The dosing elements 118 shown in FIGS. 9A to 9I are examples only, and the skilled person will understand that different parts can be added, removed, or combined to provide dosing elements 118 that provide fluid communication between at least one medicament cavity and the outlet of a mouthpiece when in a dose-administering position.

The dry powder inhalers disclosed herein provide a dosing mechanism having a dose wheel and a dosing element that allow two medicament cavities to be simultaneously accessed for delivery in a combined dose. The dosing element acts both as a mechanism for accessing the medicament cavities and delivering the medicament to the user. This allows medicaments from two separate medicament cavities to be deaggregated and mixed properly before inhalation by a user. The mechanism allows such doses to be delivered in a repeatable manner. The mechanism has a simpler construction than those currently known for provided combined doses of multiple medicaments.

The methods of packaging dry powder medicaments disclosed herein, and the packaging produced by such methods, provide for filling a number of cavities in a linear row, before being assembled into an inhaler. This allows multiple medicament cavities to be easily filled and sealed such that they can be provided in a combined dose.

As used herein, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc. do not preclude a plurality. Reference signs in the claims are provided merely as a clarifying example and shall not be construed as limiting the scope of the claims in any way.

The invention claimed is:

1. A dry powder inhaler comprising:
at least one inlet;
at least one outlet; and
a dosage mechanism between the at least one inlet and the at least one outlet for arranging a dose of a dry powder medicament such that the dose may be delivered upon inhalation at the at least one outlet, wherein the dosage mechanism comprises:
a dose wheel structured and arranged to retain a plurality of medicament cavities for housing the dry powder medicament; and
a dosing element movable between an inactive position and a dose-administering position, the dosing element structured and arranged to enable fluid communication between at least one of the plurality of medicament cavities and the at least one outlet when in the dose-administering position, wherein the dosing element is configured to at least partially remove a sealing element from two medicament cavities of the plurality of medicament cavities simultaneously when moving from the inactive position to the dose-administering position to enable fluid communication between the two medicament cavities and the at least one outlet when in the dose-administering position, and wherein each medicament cavity of the plurality of medicament cavities comprises a volume where open sides of the volumes of the two medicament cavities face each other.

2. The dry powder inhaler of claim 1, wherein the dose wheel is structured and arranged to rotate relative to the dosing element between a plurality of dose delivery positions.

3. The dry powder inhaler of claim 2, wherein each dose delivery position corresponds to an alignment between the two medicament cavities of the plurality of medicament cavities and the dosing element.

4. The dry powder inhaler of claim 1, further comprising a gear system configured to rotate the dose wheel relative to the dosing element and/or actuate the dosing element between the inactive position and the dose-administering position.

5. The dry powder inhaler of claim 4, wherein the gear system comprises a first gear mechanism and a second gear mechanism;

the first gear mechanism is configured to rotate the dose wheel;

the second gear mechanism is configured to actuate the dosing element; and the first gear mechanism and the second gear mechanism are configured to interact such that the rotation of the dose wheel and the actuation the dosing element are provided in the same action.

6. The dry powder inhaler of claim 4, wherein, in the inactive position, the dosing element is arranged within the dose wheel.

7. The dry powder inhaler of claim 1, wherein, in the inactive position, the dosing element is arranged within the dose wheel.

8. The dry powder inhaler of claim 1, wherein the dosing element comprises a manifold arranged to provide fluid communication between the at least one inlet and at least one of the plurality of medicament cavities and between the at least one of the plurality of medicament cavities and the at least one outlet when in the dose-administering position.

9. The dry powder inhaler of claim 8, wherein the manifold comprises at least one first conduit and at least one second conduit, wherein, when in the dose-administering position:

the at least one first conduit is arranged to provide fluid communication between at least one medicament cavity of the plurality of medicament cavities and the at least one second conduit; and the at least one second conduit is arranged to provide fluid communication between the at least one first conduit and the at least one outlet.

10. The dry powder inhaler of claim 9, wherein the at least one first conduit includes two first conduits, each arranged to provide fluid communication between a respective medicament cavity of the plurality of medicament cavities and the at least one second conduit when in the dose-administering position.

11. The dry powder inhaler of claim 10, wherein the at least one second conduit includes two second conduits, each arranged to provide fluid communication between the at least one first conduit and the at least one outlet when in the dose-administering position.

12. The dry powder inhaler of claim 10, wherein the manifold further comprises at least one third conduit to provide fluid communication between the at least one inlet and the at least one first conduit and/or between the at least one inlet and the at least one second conduit when in the dose-administering position.

13. The dry powder inhaler of claim 9, wherein the at least one second conduit includes two second conduits, each arranged to provide fluid communication between the at least one first conduit and the at least one outlet when in the dose-administering position.

14. The dry powder inhaler of any of claim 9, wherein the manifold further comprises at least one third conduit arranged to provide fluid communication between the at least one inlet and the at least one first conduit and/or between the at least one inlet and the at least one second conduit when in the dose-administering position.

15. The dry powder inhaler of claim 1, wherein each medicament cavity of the plurality of medicament cavities is sealed by the sealing element.

16. The dry powder inhaler of claim 15, wherein the sealing element is a film or foil.

17. The dry powder inhaler of claim 1, wherein the dosing element is configured to at least partially remove the sealing element by peeling the sealing element from the two medicament cavities when moving from the inactive position to the dose-administering position.

18. The dry powder inhaler of claim 17, wherein the sealing element is a film or foil.

* * * * *